US006410226B1

(12) United States Patent
Kmiec et al.

(10) Patent No.: US 6,410,226 B1
(45) Date of Patent: *Jun. 25, 2002

(54) MAMMALIAN AND HUMAN REC2

(75) Inventors: Eric B. Kmiec, Yardley, PA (US); William K. Holloman, Yorktown Heights, NY (US); Michael C. Rice, Newtown, PA (US); Sheryl T. Smith, Bryn Mar, PA (US); Zhigang Shu, Bensalem, PA (US)

(73) Assignees: Thomas Jefferson University, Philadelphia, PA (US); Cornell Research Foundation, Inc., Ithaca, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/927,165

(22) Filed: Sep. 11, 1997

Related U.S. Application Data

(60) Provisional application No. 60/025,929, filed on Sep. 11, 1996.

(51) Int. Cl.[7] .......................... C12Q 1/68; C12P 19/34; C07H 21/04
(52) U.S. Cl. ...................... 435/6; 435/91.1; 435/91.2; 536/23.1; 536/24.3
(58) Field of Search .................... 435/6, 91.1, 91.2; 536/24.3, 23.1

(56) References Cited

FOREIGN PATENT DOCUMENTS

WO   WO 96/22364   7/1996

OTHER PUBLICATIONS

Fan et al. "A novel link between REC2, a DNA Recombinase, the Retinoblastoma Protein, and Apoptosis": J. of Biol. Chem., vol. 272, pp. 19413–19417, Aug. 1997.*
Albala et al. "Identificataion of Novel Human RAD51 Homolog, RAD51B"; Genomics, vol. 46, pp. 476–479, 1997.*
The Human Genome, "Mapping the Human Genome", chap. 4, pp. 71–96, 1994.*
GenBank accession No.: R50193, 1995.*
GenBank accession No.: W05003, 1996.*
GenBank accession No.: T92120, 1995.*
GenBank accession No.: T92023, 1995.*
Papathanasiou et al., "Induction by Ionizing Radiation of the gadd45 Gene in Cultured Human Cells: Lack of Mediation by Protein Kinase C", Mol Cell Biol, 11, 1009–1016, (1991).
Chung et al., "DNA Mismatch Repair and Cancer", Gastroenterology, 109, 1685–1699 (1995).
Lowe et al., "p53 Status and the Efficacy of Cancer Therapy In Vivo", Science, 266, 807–810, (1994).
Bauchwitz et al., "Isolation of the REC 2 Gene Controlling Recombination in *Ustilago Maydis*", Gene, 96, 285–288, (1990).
Rubin et al., "Structure of REC 2, a Recombination Repair Gene of *Ustilago Maydis*, and its Function in Homologous Recombination Between Plasmid and Chromosomal Sequences", Mol Cell Biol, 14, 6287–6296, (1994).
Kmiec et al, "The REC2 Gene Encodes the Homologous Pairing Protein of *Ustilago Maydis*", Mol Cell Biol, 14, 7163–7172, (1994).
Rice et al., "Isolation of Human and Mouse Genes Based on Homology to REC2, a Recombinational Repair Gene from the Fungus *Ustilage Maydis*", Proc Natl Acad Sci USA, 94, 7417–7422, (1997).
Mountford et al., "Dicistronic Targeting Constructs; Reporters and Modifiers of Mammalian Gene Expression", Proc Natl Acad Sci USA, 91, 4303–4307, (1994).
Mauceri et al., "Tumor Necrosis Factor α (TNF–α)Gene Therapy Targeted by Ionizing Radiation Selectively Damages Tumor Vasculature," Cancer Research, 56, 4311–4314, Oct. 1, 1996.

* cited by examiner

*Primary Examiner*—W. Gary Jones
*Assistant Examiner*—Jehanne Souaya
(74) *Attorney, Agent, or Firm*—Drinker Biddle & Reath LLP

(57) ABSTRACT

The invention concerns mammalian recombinase genes (REC2) and their promoters. Over expression of REC2 in a cell is found to facilitate homologous recombination, particularly homologous recombination using a DNA/RNA chimeric oligonucleotide and to sensitize a cell to the apoptotic effects of irradiation. The REC2 promoter, in combination with a strong enhancer, e.g., a SV40 enhancer, was found to be a strong promoter following irradiation of the cells. A radiation induceable promoter can be used to sensitize a cell to radiation treatment by operably linking the radiation induceable promoter to a gene whose expression converts a prodrug to a drug such as a herpes thymidien kinase gene.

10 Claims, 24 Drawing Sheets

Figure 2B:
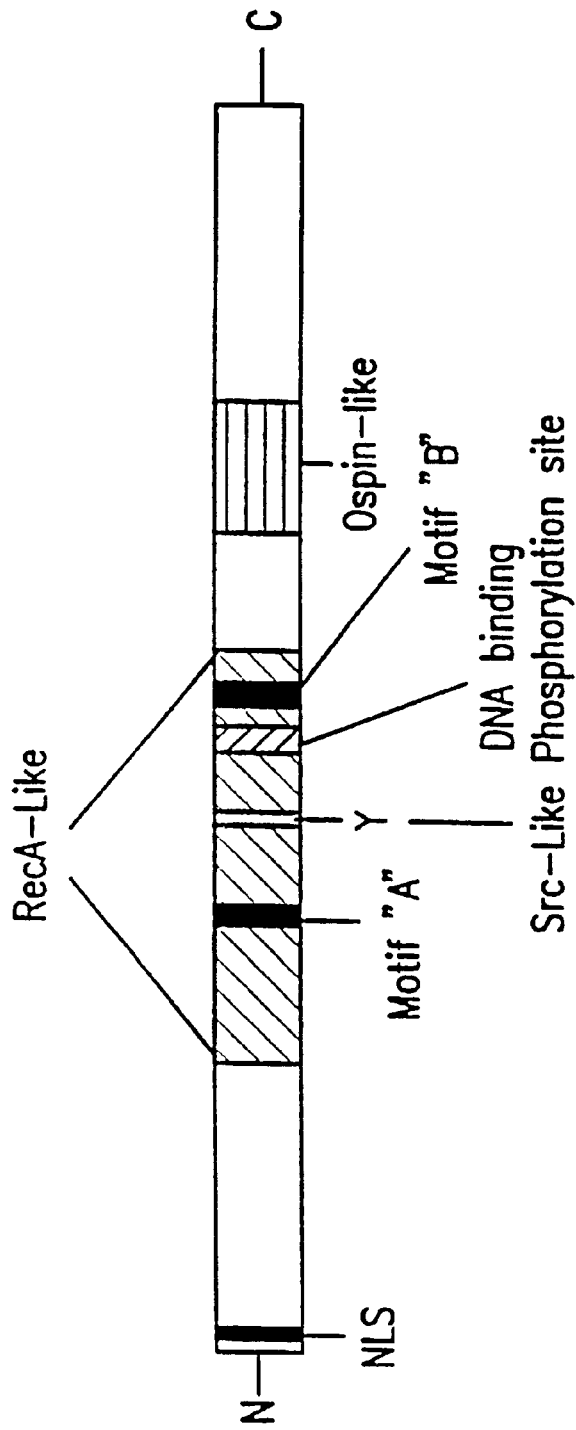

```
Met Gly Ser Lys Lys Leu Lys Arg Val Gly Leu Ser Gln Glu Leu Cys
 1                   5                  10                  15
Asp Arg Leu Ser Arg His Gln Ile Leu Lys Arg Val Gly Leu Ser Gln
                20                  25                  30
Leu Ser Pro Leu Glu Leu Met Lys Val Thr Gly Leu Ser Ala Pro Lys Met
                35                  40                  45
Val His Glu Leu Leu Cys Met Val Ser Arg Ala Cys Ala Pro Lys Met
                50                  55                  60
Gln Thr Ala Tyr Gly Ile Lys Ala Gln Arg Ser Ala Asp Phe Ser Pro
 65                 70                  75                  80
Ala Phe Leu Ser Thr Thr Leu Ser Ala Leu Asp Glu Ala Leu His Gly
                85                  90                  95
Gly Val Ala Cys Gly Ser Leu Thr Glu Ile Thr Gly Pro Pro Gly Cys
                100                 105                 110
Gly Lys Thr Gln Phe Cys Ile Met Met Ser Ile Leu Ala Thr Leu Pro
 115                120                 125
Thr Asn Met Gly Gly Leu Glu Gly Ala Val Val Tyr Ile Asp Thr Glu
 130                135                 140
Ser Ala Phe Ser Ala Glu Arg Leu Val Glu Ile Ala Glu Ser Arg Phe
 145                150                 155                 160
Pro Arg Tyr Phe Asn Thr Glu Glu Lys Leu Leu Leu Thr Ser Ser Lys
                165                 170                 175
```

FIG.1A

```
Val His Leu Tyr Arg Glu Leu Thr Cys Asp Glu Val Leu Gln Arg Ile
                180                 185                 190
Glu Ser Leu Glu Glu Glu Ile Ile Ser Lys Gly Ile Lys Leu Val Ile
            195                 200                 205
Leu Asp Ser Val Ala Ser Val Arg Lys Glu Phe Asp Ala Gln Leu
        210                 215                 220
Gln Gly Asn Leu Lys Glu Arg Asn Lys Phe Leu Ala Arg Glu Ala Ser
            225                 230             235                 240
Ser Leu Lys Tyr Leu Ala Glu Glu Phe Ser Ile Pro Val Ile Leu Thr
            245                 250                 255
Asn Gln Ile Thr Thr His Leu Ser Gly Ala Leu Ala Ser Gln Ala Asp
            260                 265                 270
Leu Val Ser Pro Ala Asp Asp Leu Ser Leu Ser Glu Gly Thr Ser Gly
            275                 280                 285
Ser Ser Cys Val Ile Ala Ala Leu Gly Asn Thr Trp Ser His Ser Val
        290                 295                 300
Asn Thr Arg Leu Leu Ile Leu Gln Tyr Leu Asp Ser Glu Arg Arg Gln Ile
305                 310                 315                 320
Leu Ile Ala Lys Ser Pro Leu Ala Pro Phe Thr Ser Phe Val Tyr Thr
            325                 330                 335
Ile Lys Glu Gly Leu Val Leu Gln Ala Tyr Gly Asn Ser
            340                 345                 350
```

FIG.1B

```
CGGACGCGTG GGCGCGGGGA AACTGTGTAA AGGGTGGGGA AACTTGAAAG TTGGATGCTG   60
CAGACCCGGC ATGGGTAGCA AGAAACTAAA ACGAGTGGGT TTATCACAAG AGCTGTGTGA  120
CCGTCTGAGT AGACATCAGA TCCTTACCTG TCAGGACTTT TTATGTCTTT CCCCACTGGA  180
GCTTATGAAG GTGACTGGTC TGAGTTATCG AGGTGTCCAT GAACTTCTAT GTATGGTCAG  240
CAGGGCCTGT GCCCCAAAGA TGCAAACGGC TTATGGGATA AAAGCACAAA GGTCTGCTGA  300
TTTCTCACCA GCATTCTTAT CTACTACCCT TTCTGCTTTG GACGAAGCCC TGCATGGTGG  360
TGTGGCTTGT GGATCCCTCA CAGAGATTAC AGGTCCACCA GGTTGTGGAA AAACTCAGTT  420
TTGTATAATG ATGAGCATTT TGGCTACATT ACCCACCAAC ATGGGAGGAT TAGAAGGAGC  480
TGTGGTGTAC ATTGACACAG AGTCTGCATT TAGTGCTGAA AGACTGGTTG AAATAGCAGA  540
ATCCCGTTTT CCCAGATATT TTAACACTGA AGAAAAGTTA CTTTTGACAA GTAGTAAAGT  600
TCATCTTTAT CGGGAACTCA CCTGTGATGA AGTTCTACAA AGGATTGAAT CTTTGGAAGA  660
AGAAATTATC TCAAAAGGAA TTAAACTTGT GATTCTTGAC TCTGTTGCTT CTGTGGTCAG  720
AAAGGAGTTT GATGCACAAC TTCAAGGCAA TCTCAAAGAA AGAAACAAGT TCTTGGCAAG  780
AGAGGCATCC TCCTTGAAGT ATTTGGCTGA GGAGTTTTCA ATCCCAGTTA TCTTGACGAA  840
TCAGATTACA ACCCATCTGA GTGGAGCCCT GCAGACCTGG GCTTCTCCAG TGTCTCCAGC  900
```

FIG. 1C

```
TGATGATTTG  TCCCTGTCTG  AAGGCACTTC  TGGATCCAGC  TGTGTGATAG  CCGCACTAGG   960
AAATACCTGG  AGTCACAGTG  TGAATACCCG  GCTGATCCTC  CAGTACCCTG  ATTCAGAGAG  1020
AAGACAGATT  CTTATTGCCA  AGTCCCCTCT  GGCTCCCTTC  ACCTCATTTG  TCTACACCAT  1080
CAAGGAGGAA  GGCCTGGTTC  TTCAAGCCTA  TGGAAATTCC  TAGAGACAGA  TAAATGTGCA  1140
AACCTGTTCA  TCTTGCCAAG  AAAAATCCGC  TTTCTGCCA   CAGAAACAAA  ATATTGGGAA  1200
AGAGTCTTGT  GGTGAAACAC  CCATCGTTCT  CTGCTAAAAC  ATTTGGTTGC  TACTGTGTAG  1260
ACTCAGCTTA  AGTCATGGAA  TTCTAGAGGA  TGTATCTCAC  AAGTAGGATC  AAGAACAAGC  1320
CCAACAGTAA  TCTGCATCAT  AAGCTGATTT  GATACCATGG  CACTGACAAT  GGGCACTGAT  1380
TGATACCAT   GGCACTGACA  ATGGGAACAGG  AAATGGGAAT  CACTGACAAT  GAGAGCAAGG  1440
GTTGGGTTGT  GTTCGTGGAA  CACATAGTT   TTTTTTTTA   ACTTTCTCTT  TCTAAAATAT  1500
TTCATTTTGA  TGGAGGTGAA  ATTTATATAA  GATGAAATTA  ACCATTTTAA  AGTAAACAAT  1560
TCCGTGGCAA  CTAGATATCA  TGATGTGCAA  CCAGCATCTC  TGTCTAGTTC  CCAAATATTT  1620
CATCACCCCC  AAAAGCAAGA  CCCATAACCA  TTATGCAAGT  GTTCCTATTT  CCCCCCTC    1680
CCAGCTCCTG  GGAAACCACC  AATCTACTTT  TTTTCTATGG  CTTTACCTAA  TCTGGAAATT  1740
TCAAATAAAT  GGGATCAAAT  AGTTTCCCAA  AAAAAAAAAA  AAAAAAAAAA  AAAAAAA     1797
```

FIG.1D

```
Met Ser Ser Lys Lys Leu Arg Arg Val Gly Leu Ser Pro Glu Leu Cys
  1               5                      10                  15
Asp Arg Leu Ser Arg Tyr Leu Ile Val Asn Cys Gln His Phe Leu Ser
             20                  25                  30
Leu Ser Pro Leu Glu Leu Met Lys Val Thr Gly Leu Ser Tyr Arg Gly
         35                  40                  45
Val His Glu Leu Leu His Thr Val Ser Lys Ala Cys Ala Pro Gln Met
     50                  55                  60
Gln Thr Ala Tyr Glu Leu Lys Thr Arg Arg Ser Ala His Leu Ser Pro
 65                  70                  75                  80
Ala Phe Leu Ser Thr Thr Leu Cys Ala Leu Asp Glu Ala Leu His Gly
                 85                  90                  95
Gly Val Pro Cys Gly Ser Leu Thr Glu Ile Thr Gly Pro Pro Gly Cys
             100                 105                 110
Gly Lys Thr Gln Phe Cys Ile Met Met Ser Val Leu Ala Thr Leu Pro
         115                 120                 125
Thr Ser Leu Gly Gly Leu Glu Arg Leu Val Val Tyr Ile Asp Thr Glu
     130                 135                 140
Ser Ala Phe Thr Ala Glu Arg Leu Val Glu Ile Ala Glu Ser Arg Phe
 145                 150                 155                 160
Pro Gln Tyr Phe Asn Thr Glu Glu Lys Leu Leu Leu Thr Ser Ser Arg
                 165                 170                 175
```

FIG.1E

```
Val His Leu Cys Arg Glu Leu Thr Cys Glu Gly Leu Leu Gln Arg Leu
            180                 185                 190
Glu Ser Leu Glu Glu Glu Ile Ile Ser Lys Gly Val Lys Leu Val Ile
            195                 200             205
Val Asp Ser Ile Ala Ser Val Arg Lys Glu Phe Asp Pro Lys Leu
            210                 215                 220
Gln Gly Asn Ile Lys Glu Arg Asn Lys Phe Leu Gly Lys Gly Ala Ser
            225                 230             235             240
Leu Leu Lys Tyr Leu Ala Gly Glu Phe Ser Ile Pro Val Ile Leu Thr
            245                 250                 255
Asn Gln Ile Thr Thr His Leu Ser Gly Ala Leu Pro Ser Gln Ala Asp
            260                 265                 270
Leu Val Ser Pro Ala Asp Asp Leu Ser Leu Ser Glu Gly Thr Ser Gly
            275                 280             285
Ser Ser Cys Leu Val Ala Ala Leu Gly Asn Thr Trp Gly His Cys Val
            290                 295             300
Asn Thr Arg Leu Ile Leu Gln Tyr Leu Asp Ser Glu Arg Arg Gln Ile
            305                 310             315                 320
Leu Ile Ala Lys Ser Pro Leu Ala Ala Phe Thr Ser Phe Val Tyr Thr
            325                 330                 335
Ile Lys Gly Glu Gly Leu Val Leu Gln Gly His Glu Arg Pro
            340                 345             350
```

FIG.1F

```
GGGAGCCCTG GAAACATGAG CAGCAAGAAA CTAAGACGAG TGGGTTTATC TCCAGAGCTG    60
TGTGACCGTT TAAGCAGATA CCTGATTGTT AACTGTCAGC ACTTTTTAAG TCTCTCCCCA   120
CTAGAACTTA TGAAAGTGAC TGGCCTGAGT TACAGAGGTG TCCACGAGCT TCTTCATACA   180
GTAAGCAAGG CCTGTGCCCC GCAGATGCAA ACGGCTTATG AGTTAAAGAC ACGAAGGTCT   240
GCACATCTCT CACCGGCATT CCTGTCTACT ACCCTGTGCG CCTTGGATGA AGCATTGCAC   300
GGTGGTGTGC CTTGTGATC  TCTCACAGAG ATTACAGGTC CACCAGGTTG CGGAAAAACT   360
CAGTTTGCA  TAATGATGAG TGTCTTAGCT ACATTACCTA CCAGCCTGGG AGGATTAGAA   420
GGGGCTGTGG TCTACATCGA CACAGAGTCT GCATTTACTG CTGAGAGACT GGTTGAGATT   480
GCGGAATCTC GTTTCCACA  ATATTTTAAC ACTGAGGAAA AATTGCTTCT GACCAGCAGT   540
AGAGTTCATC TTTGCCGAGA GCTCACCTGT GAGGGGCTTC TACAAAGGCT TGAGTCTTTG   600
GAGGAAGAGA TCATTTCGAA AGGAGTTAAG CTTGTGATTG TTGACTCCAT TGCTTCTGTG   660
GTCAGAAAGG AGTTTGACCC GAAGCTTCAA GGCAACATCA AAGAAAGGAA CAAGTTCTTG   720
GGCAAAGGAG CGTCCTTACT GAAGTACCTG GCAGGGGAGT TTTCAATCCC AGTTATCTTG   780
ACGAATCAAA TTACGACCCA TCTGAGTGGA GCCCTCCCTT CTCAAGCAGA CCTGGTGTCT   840
CCAGCTGATG ATTTGTCCCT GTCTGAAGGC ACTTCTGGAT CCAGCTGTTT GGTAGCTGCA   900
CTAGGAAACA CATGGGGTCA CTGTGTGAAC ACCCGGCTGA TCTCCAGTA  CCTTGATTCA   960
GAGAGAAGGC AGATTCTCAT TGCCAAGTCT TGCCTCACCTG CCTTCACCTC CTTTGTCTAC  1020
ACCATCAAGG GGGAAGGCCT GGTTCTTCAA GACCATAGGG ATACTGTGAC  1080
CTTTGTCTAG TGCTGATTGC ATGTGACTCA TGAAATGAAA CAGGACTGCG CTGCTTGGAA  1140
AAGGAAAACG GAAGCCAACA TAATTGGTTG GTTGCTGTTG ATCCAGTCTC AGGTGGTAAC  1200
AGTGATTTCA GACCCGGAAG GTGAAGATGA AGAAGCCTTT ATCCAGTCTC TGGATGCAGA  1260
GGCTAGGGGC TCCACCACCG TGGGATGTCA GCGGCCCATCG TAATAATTTG CACTTACACA  1320
AGCACCTTTC AGCCATGCCC CTCAAAGTGG TTCAGCCACA TAATTAATT  AAAGCCCACA  1380
ATCCCCCTAG GGAGAGCAGG AGGGGACTA  ACAAGATTTG TAATTACAGA AGGAAAATT   1440
.TCCGAATAAA AAAAAAAAAA GTATTGTTCC GCCAAAAAAA AAAAAAAAAA AAAAAAAAA   1500
AAAAAAAAAA AAAAAAAAAA AAAAA                                        1525
```

FIG.1G

MGSKKLKRVGLSQELCDRLSRHQILTCQDFLCLSPLELMKVTGLS
　　NLS
YRGVHELLCMVSRACAPKMQTAYGIKAQRSADFSPAFLSTILSA
　　　　　　　　　　　　　　　　　　　　　50
LDEALHGGVACGSLTEITGPPGCGKIQFCIMMSILATLPTNMGGL
　　　　　　　　100　　A BOX
EGAVVYIDTESAFSAERLVEIAESREPRYFNTEEKLLLTSSKVHLY
　　　　　　　　　　　150　　　　　　　P
RELTCDEVLQRIESLEEEIISKGIKLVILDSVASVVRKEFDAQLQG
　　DNA　　　　　200　　B BOX
NLKERNKFLAREASSLKYLAEEFSIPVILTNQITTHLSGALASQAD
　　　　　　　　　　　　　250
LVSPADDLSLSEGTSGSSCVIAALGNTWSHSVNTRLILQYLDSERR
　　　　　　　　　　　　　　　　300
QILIAKSPLAPFTSFVYTIKEEGLVLQAYGNS*
　　　　　　　350

FIG.2A 1 cm = 33 amino acids

```
U.m.    124  LNDARFASSCIVPPTQGYDGNFPGAQCFVYDSDAGSDSDARSSIDAVMHE  173
              :  :  |.::  .|.:: :| .:|:
Human     1  MGSKKLKR...VGLSQELCDRLSRHQILTCQDFLCLSPLELMKVTGLSYR   47

174  DI.ELPSTFCRPQTHDVARDEHHDGYLCDPKVDHASVARDVLSLGRQ    222
              ::   |.:.:|: .:|:                |:|::||||.:||:.
         48  GVHELLCMVSRA..........................CAPKMQTAYGIKAQRSADFS  79

223  RHVFSSGSRELDDLLGGGVRSAVLTELVGESGSGKTQMAIQVCTYAALGL   272
              .: .|:::| | ||  :: ||:.|:|.|:::|:.|:|||:
         80  PAFLSTTLSALDEALHGGVACGSLTEITGPPGCKTQFCIMMSILATL..   127

273  VPLSQADDHDKGNNTFQSRTFVRDPIHASTKDDTLSDILQSYGMEPSIGS  322
                                                  .:  :|.:|
        128  ..............................PTNMGGLEG..........  136

323  HRGMGACYITSGGERAAHSIVNRALELASFAINERFDRVYPVCDPTQSSQ  372
              .:|| :.:|:..:|:  |:   |
        137  ....AVVYIDTESAFSAERLVEIA..............ESRFPRYF....  164

373  DADGRRDALLAKAQQLGRRQALANLHIACVADVEALEHALKYSLPGLIRR  422
              ||          :. .|:    ..|:|.:|:
        165  ...NTEEKLLLTSSKVHLYRELTCDEV..LQRIESLEEEI..........  199

FIG.2C
```

```
423 LWSSKRQSGVSREIGVVVVDNLPALFQQDQAAASDIDSLFQRSKMLVEIA 472
     :|:::| :|:::|:::.:  |   . :  . :.:.:|. 
200 ...........ISKGIKLVILDSVASVVRKEFDAQLQ.GNLKERNKFLAREA 239

473 DALKRISAVQWRGASDCGSSAGRAVLVLNHVSDAFGIDKQIARRFVFDSA 522
                                :: :|: ::  :|. ::
240 SSLK.....................YLAEEFSIPVILTNQITTHL..... 263

573 SGLLASIAPTLAEAVGARELDSACASNDVPLRTLEARTAQLGQTWSNLIN 622
    || ||| |:|. | |  .:| ::  :|   |.|:|||:|| 
264 SGALASQADLVSPADDLSLSEGTSGSSCV...........IAALGNTWSHSVN 305

623 VRVFL......SKTRARICMRDDQAPACEPVRQNTNQRGTASKSLMNTVRKA 668
     | :| .:  |: |: |:
306 TRLILQYLDSERRQILIAKSPLAP.................FTSFVYTIKEE 340

669 AVVINPFGAT 678
    ::.||.:|.:
341 GLVLQAYGNS 350
```

FIG.2D

```
  1  CGACGGCCCG GGCTGGTATT ATAGCAGTA TCACTTGGTT TTCTACTGGG
 51  GGAAACAAGT CATTGCTAAC AAATTCCCAT GGGAGAGAAA TGAGGAGGAT
101  GTATTTTTGT TTGTGAGAGG TGTGTATGTA TGTATATTGT GTGTGCGTGT
                               <URS>
151  GTGTGTGTGT GAGAGAGAGA GATTGATTCA GTCTGATTCA GAGAATTTAG  RHP51-URS
201  GTGTTAAATA GAAATTTGGG CCATGGTATT GGAAATAAAC AAATATATAC
251  ATTCTCAGTA TACATATATT TTCATTCCAA AATGTTACTT CTTTTCTGAT
301  AACTATATTG CTTTATTCCC TTGGATCCAT GAAGAGTTCC TGTTTCAGTT
351  CGTTCCAGAG GATACTTCTT TACCATCTCA ATGAGATATA CAGCTTCTCC
     RHP51-URS
401  TTTGTATGCA TTAAGAGACT CACAGTAATT CTTTTTTAGC TCTGTGAAGA
     PHR1-UAS
451  TAAATCTTTC ATGAGCCTCA TTTACCCCTA GCAAAGTACA ATAGTGAAAT
                                                RAD23
501  TTAACTGCAT GTGAGAATAT AAGCAGCTAG TGTAATAAAG AACATTTTGG
551  GCCAGGTCTG ATCGCTCATG CCTGTAATCC CAGCACTTTA GGAGGTCAAG
601  GCGAGAGGAT CACTTGAGCC CAGGAGTTCG AGACCAGCTT GGGCAACATG
                         RAD16-URS
651  GCAAAACCCT GTCTCTACAA AAAATACAAA AATTGGGCAG GCATGGTGTC
```

FIG. 7A

```
 701  GACCCAGTCT CTACAAAAAA TACAAAAATT AGCCAGACAT GGTGGTGCAC
                                                 RAD 51-URS
 751  GCTTGTGGTC CCAGCTACTT GGGAGGCTGA GGTAGGAGGA TTGCTTGAGC
 801  CCAGGAGGGG GAGGTTGCAG TGAGCTGAGA TCGAGCCCACT GCACTCCAGC
                             RNR3-UAS
 851  TGGGGTGACA GAGCCAGACC TGTCTCGCTC TCTCTCTCTC TCTATATATA
                           <PHR1-UES>              RHP51-URS
                                        PHR1-URS
 901  TATATTTAAA AAGAACATT TAATACTGCA GTGATAAAAT CTCATTTGAT
 951  TCAGAAGGTG TGCTCTGACT CCTAGAAAAA GGAAGAGTCA AATATGATTA
1001  TGGACTTGCA GTAGAGTGTA ATGGTTAAGA GGATAGGTTT CAGAATTAGA
1051  CTGCCTGGAT TCAAATTCTG GCTTTAGTTT TCTCATATGT AAAAAAGGGG
1101  GGACTAGCTA ACTTTTCCAG GCTTTAGTTT TCTCATATGT AAAAAAGGGG
      RHP51-URS
1151  CCAATAATCT ACTTCCTTC TAGGGCTATT GAGAAGATTA AATGTGATAA
                 RHP51-UAS
1201  TTTAGATAAG TTTTGGAACA GTGCCCTGGTA GTGGTAGGT GCTCCATAAA
1251  TATACCTATT GCCGTTACAG ATGTTACAG TGCAATAGAC
              RAD54-UAS
1301  TTTCTAGTAG TTCTGTTTGG AAATATGCCT TGAAAGTTAA TTACATTCC RAD54-URS
1351  AAATAAAAATT TATACATGCA TGGAACATT TTAAGATGCT CTACAAATGT
1401  GAAGTGGTAC TATATTCATG TAGTAAATAT CAATTAATTG TGTGAAATTA URS (PHR1)
```

FIG. 7B

```
1451  TATTTGAGGT TGCCTTGTAG ATTTTCTATG TGCCTGTTTG ACGAACAATT
                 RNR3-UAS
1501  GTCCCTCCTA TTTAAAAACAT TTAAAAAGGT TCTATAGCAT TCCTTTATCA
1551  GTAATATTTT TAACACAATA TGTTTCATTT TGCATATGGA GAAACTTGAG
                                                  RAD23-UAS
1601  GAATTTTTAA TTTGTTTTG GATAGCCTAT TCACTATCAC TTATGTTATA
      PHR1-URS           RAD51-UAS                        TATA BOX
                              RNR3-UAS
                                    RHP51-UAS
1651  TTCTGTTGTT TTTTTCATGG TTCTTCTTTT CTTTGCTGGA TCTGGAGGC
      <PHR1-UAS> (OVERLAP WITH DRE2)
```

FIG.7C

```
  1 TATCTCAGTA GCACGTGCAC ATAGCAACTA CAATACCTGT CACATAAATG
               RNR3
 51 TAGTTACTTG AATATATGTC TCTTCATTCT TCAATTGTAA GTATGCAAAA
101 GGGAGGACAT AAGCTTAGCA TAGCATGTGC TTAATATTGG TGAAAGAAAC  <RAD6>
                                                RAD23
151 AAATGAATAG AGAATGTTAT ATTGGAGAG TTTATATTAT ATTTGGGAGA
201 GTAGGGAAAA AACTTGAAGC CATAAGCAGA ATCGAGGGCA AGTAGTGAGA
251 GTGGTACTGT TAAATCAGAG TGATTATTGC TAAGGTCTTT GTAATTTGGG
301 GTTGTAGGTG TTTTTTGTTT TTGTTGTTTG AGGGTCTGAA TTTATTCGTT
               RHP51                RNR3
351 ATATGATGTT ATTGCCTGGA ACTACCTTAT CTGAGAAGCA GTAGGCAATA
                         RAD51-UAS
401 GAGTAGCGTA TAAATGTTGG TAAATTTTCT CTTAAGGAAA CAAATTATCC
                                              RAD7
451 TTACAAAATT CCAACTGAAA GAAATAAAGA GAATGTATCT TGGTTTTGTG
    RAD54-UAS
501 TGGAGAGAGG GAAGTAGAAG ATGGGGGATG AAGAGAGAGA GGAGGGTTAT
    RAD-1
551 TTATTGGGCT ATATATAGTG TTGGTAGTAG GAATCTTAAT TCTTGTGTGT
601 AGTTTTGTTC TTTGTGTAT AGTTATTGAT TATTACTTTA TTCCATGGGA
651 ATAATGAGTT CCTATTATTT CTGGAGGATA TTTTGCCATT TCGATGAGAC
701 ACACAGCCCTC TTCTTTGCTA TGCAATATTA CGAGATTACA ACAGTTCTAA
```

FIG.7D

```
 751  CTCCCTGAAG ACAAATACTT CATGAGTCTC ATTAGCTATC TAAGCTATAG  PHR1-1
 801  GAAGAGCAGA ATTTAATTCT ACATGGAAAC AGTAAGAAGC TAGTATAATG
                            PHR1-UAS
 851  AAGAATTTTA TTGATATCAC TTGATTGAAA TTTGTTCTGA CTCTTTAGAA
 901  AAAGCAAGGG TGAAATAAGA TTTGTGATTC TACAGTAGTA ATGGGTAAGA
 951  GGATAGGTCT CAGGACAAAC TGCCTAATGA AACCCTAAAT CTGTTATTTA
                                       RHP51-UAS
1001  TTTATTTTCT GATGACAGTG GGATAACTGA CATTTACACA TTAGCTTTCT
1051  CATATGTAAA AAAGAAATTT TATTTTTATT ATAGTCTGTC AAGGAATATT
1101  AAATATAAGG TTTGGAGCA TGGTTGATAT TTAGCAGATG TCTGTTCATT
                      RNR3-1
                              RAD16-1
1151  CTTGATCAGT ATAGAGTTGC CACTTGGAAA ATGCATCTTG AAGATTACAT
1201  AACCAGACAA AATTTGTTAG TAACACTCAG TGGTCTTAAG ATGTTATAAG
                                  <RAD16>
1251  TGACGGGCTA GTCGTGGTAA TCAACTTGAT ACCTTGACCC TCAGGAGAAG
                       <DRE2>
1301  AGGGATTGTC TCCATCGGAT GGGCCTGTGA GCATATCTGT GGGGACGTT̥
1351  TTCTTGGACT GCCTAGTTGA TGGAAAAGGG CTTGGCTCAG TGTCAGTGGT
1401  CCTTCTTATG GTGAGCAAGC TGGGGGAAGC GTTGCAGTAA GCAGTAGTCC
                                                PHR1-UAS
1451  TTGTGGGTCT CAGCTTCCTT TTCTTCTCTC TTCTTTCTTT CTTTCTTTCT
```

FIG. 7E

```
1501  TTCTTTCTTT CTTTCTTTCT TTCTTCCTTC CTTCCTTCCT TTTCTCTCTT
                                                 RHP51-UAS
1551  TCTTTCTTTA GTTCCGTTCG TTTGTTCATT CGTCGTTTT TCGAGACAGG
                 RHP51-UAS                       <UAS>
1601  GTTTTTCTGT ATAGCCCTGG CTGTCCTGGA ACTCACTTTG TAGACCAGGC
1651  TGTCCCTCGAA CTCAGAAATC CGCCTGCCTC TGCCTCCCTG TGAGTGCTGG  RAD2-UAS
1701  AATTAAAGGC ATGCGCCACC CCGCCCGGCT TCTCAGCTTC CATTTCTGTT
1751  CAAGCTCTTG CCTTCAGCTC CTGCCTTGGC TTTCTGAGAC AAAGGCATAT
1801  AATCTGTAAG CCAAATCAAA CTTTTTCTTCT CAACTTGCTT TTGGCCAGTG
1851  TTTTATTACA GCGACTAAAG GCAAACTAGA CTACTATGTA AATGGGAAGC  PHR1
                                                 RHP51-2
1901  ACTGTTAAAG TCAAGTAATA GCAAAAGATT ACATGGCCTG GATTTTTGA
      RNR2
1951  GGTTGCTTAC TTTCTCTGTG TATCCGGTTG TAAGTGTCTT TCCTACTTTT
      RPH51-UAS
2001  TTTATTAGCA TTTTTTTTCC ATGTTTTGCT TTGCACATAG AGAAGTTTGA
                                                 <DRS>
2051  AGCACTTTAT TTTGTAGGGT GTTTTGTATA ATCTGTCCAC CATCATTTTT
2101  ATTGTTTTCT TATGTTTTTT CAAGATTTCT TTGGGAGCCC TGGAAAC
```

FIG.7F

SEQUENCE LISTING (1) GENERAL INFORMATION:

(iii) NUMBER OF SEQUENCES: 39

(2) INFORMATION FOR SEQ ID NO:1:

(i) SEQUENCE CHARACTERISTICS:
    (A) LENGTH: 350 amino acids
    (B) TYPE: amino acid
    (C) STRANDEDNESS: single
    (D) TOPOLOGY: linear (xi) SEQUENCE DESCRIPTION: SEQ ID NO:1:

```
Met Gly Ser Lys Lys Leu Lys Arg Val Gly Leu Ser Gln Glu Leu Cys
 1               5                  10                  15
Asp Arg Leu Ser Arg His Gln Ile Leu Thr Cys Gln Asp Phe Leu Cys
                20                  25                  30
Leu Ser Pro Leu Glu Leu Met Lys Val Thr Gly Leu Ser Tyr Arg Gly
                35                  40                  45
Val His Glu Leu Leu Cys Met Val Ser Arg Ala Cys Ala Pro Lys Met
     50                  55                  60
Gln Thr Ala Tyr Gly Ile Lys Ala Gln Arg Ser Ala Asp Phe Ser Pro
 65                  70                  75                  80
Ala Phe Leu Ser Thr Thr Leu Ser Ala Leu Asp Glu Ala Leu His Gly
                85                  90                  95
Gly Val Ala Cys Gly Ser Leu Thr Glu Ile Thr Gly Pro Pro Gly Cys
                100                 105                 110
Gly Lys Thr Gln Phe Cys Ile Met Met Ser Ile Leu Ala Thr Leu Pro
                115                 120                 125
Thr Asn Met Gly Gly Leu Glu Gly Ala Val Val Tyr Ile Asp Thr Glu
    130                 135                 140
Ser Ala Phe Ser Ala Glu Arg Leu Val Glu Ile Ala Glu Ser Arg Phe
145                 150                 155                 160
Pro Arg Tyr Phe Asn Thr Glu Glu Lys Leu Leu Leu Thr Ser Ser Lys
                165                 170                 175
Val His Leu Tyr Arg Glu Leu Thr Cys Asp Glu Val Leu Gln Arg Ile
                180                 185                 190
Glu Ser Leu Glu Glu Glu Ile Ile Ser Lys Gly Ile Lys Leu Val Ile
                195                 200                 205
Leu Asp Ser Val Ala Ser Val Val Arg Lys Glu Phe Asp Ala Gln Leu
    210                 215                 220
Gln Gly Asn Leu Lys Glu Arg Asn Lys Phe Leu Ala Arg Glu Ala Ser
225                 230                 235                 240
Ser Leu Lys Tyr Leu Ala Glu Glu Phe Ser Ile Pro Val Ile Leu Thr
                245                 250                 255
Asn Gln Ile Thr Thr His Leu Ser Gly Ala Leu Ala Ser Gln Ala Asp
                260                 265                 270
Leu Val Ser Pro Ala Asp Asp Leu Ser Leu Ser Glu Gly Thr Ser Gly
                275                 280                 285
Ser Ser Cys Val Ile Ala Ala Leu Gly Asn Thr Trp Ser His Ser Val
                290                 295                 300
Asn Thr Arg Leu Ile Leu Gln Tyr Leu Asp Ser Glu Arg Arg Gln Ile
305                 310                 315                 320
Leu Ile Ala Lys Ser Pro Leu Ala Pro Phe Thr Ser Phe Val Tyr Thr
                325                 330                 335
Ile Lys Glu Glu Gly Leu Val Leu Gln Ala Tyr Gly Asn Ser
                340                 345                 350
```

(2) INFORMATION FOR SEQ ID NO:2:

(i) SEQUENCE CHARACTERISTICS:
        (A) LENGTH: 1797 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:2:

```
CGGACGCGTG GGCGCGGGGA AACTGTGTAA AGGGTGGGGA AACTTGAAAG TTGGATGCTG      60
CAGACCCGGC ATGGGTAGCA AGAAACTAAA ACGAGTGGGT TTATCACAAG AGCTGTGTGA     120
CCGTCTGAGT AGACATCAGA TCCTTACCTG TCAGGACTTT TTATGTCTTT CCCCACTGGA     180
GCTTATGAAG GTGACTGGTC TGAGTTATCG AGGTGTCCAT GAACTTCTAT GTATGGTCAG     240
CAGGGCCTGT GCCCCAAAGA TGCAAACGGC TTATGGGATA AAGCACAAA GGTCTGCTGA      300
TTTCTCACCA GCATTCTTAT CTACTACCCT TTCTGCTTTG GACGAAGCCC TGCATGGTGG     360
TGTGGCTTGT GGATCCCTCA CAGAGATTAC AGGTCCACCA GGTTGTGAA AAACTCAGTT      420
TTGTATAATG ATGAGCATTT TGGCTACATT ACCCACCAAC ATGGGAGGAT TAGAAGGAGC     480
TGTGGTGTAC ATTGACACAG AGTCTGCATT TAGTGCTGAA AGACTGGTTG AAATAGCAGA    540
ATCCCGTTTT CCCAGATATT TTAACACTGA AGAAAGTTA CTTTTGACAA GTAGTAAAGT     600
TCATCTTTAT CGGGAACTCA CCCTGTGATGA AGTTCTACAA AGGATTGAAT CTTTGGAAGA   660
AGAAATTATC TCAAAAGGAA TTAAACTTGT GATTCTTGAC TCTGTTGCTT CTGTGGTCAG    720
AAAGGAGTTT GATGCACAAC TTCAAGGCAA TCTCAAAGAA AGAAACAAGT TCTTGGCAAG    780
AGAGGCATCC TCCTTGAAGT ATTTGGCTGA GGAGTTTTCA ATCCCAGTTA TCTTGACGAA    840
TCAGATTACA ACCCATCTGA GTGGAGCCCT GGCTTCTCAG GCAGACCTGG TGTCTCCAGC    900
TGATGATTTG TCCCTGTCTG AAGGCACTTC TGGATCCAGC TGTGTGATAG CCGCACTAGG    960
AAATACCTGG AGTCACAGTG TGAATACCCG GCTGATCCTC CAGTACCTTG ATTCAGAGAG   1020
AAGACAGATT CTTATTGCCA AGTCCCTCT GGCTCCCTTC ACCTCATTTG TCTACACCAT    1080
CAAGGAGGAA GGCCTGGTTC TTCAAGCCTA TGGAAATTCC TAGAGACAGA TAAATGTGCA   1140
AACCTGTTCA TCTTGCCAAG AAAAATCCGC TTTTCTGCCA CAGAAACAAA ATATTGGGAA   1200
AGAGTCTTGT GGTGAAACAC CCATCGTTCT CTGCTAAAAC ATTTGGTTGC TACTGTGTAG   1260
ACTCAGCTTA AGTCATGGAA TTCTAGAGGA TGTATCTCAC AAGTAGGATC AAGAACAAGC   1320
CCAACAGTAA TCTGCATCAT AAGCTGATTT GATACCATGG CACTGACAAT GGGCACTGAT   1380
TTGATACCAT GGCACTGACA ATGGGCACAC AGGGAACAGG AAATGGGAAT GAGAGCAAGG   1440
GTTGGGTTGT GTTCGTGGAA CACATAGGTT TTTTTTTTTA ACTTTCTCTT TCTAAAATAT   1500
TTCATTTTGA TGGAGGTGAA ATTTATATAA GATGAAATTA ACCATTTTAA AGTAAACAAT   1560
TCCGTGGCAA CTAGATATCA TGATGTGCAA CCAGCATCTC TGTCTAGTTC CCAAATATTT   1620
CATCACCCCC AAAAGCAAGA CCCATAACCA TTATGCAAGT GTTCCTATTT CCCCCTCCTC   1680
CCAGCTCCTG GGAAACCACC AATCTACTTT TTTTCTATGG CTTTACCTAA TCTGGAAATT   1740
TCAAATAAAT GGGATCAAAT AGTTTCCCAA AAAAAAAAAA AAAAAAAAAA AAAAAA       1797
```

(2) INFORMATION FOR SEQ ID NO:3:

(i) SEQUENCE CHARACTERISTICS:
(A) LENGTH: 350 amino acids
(B) TYPE: amino acid
(C) STRANDEDNESS: single
(D) TOPOLOGY: linear (xi) SEQUENCE DESCRIPTION: SEQ ID NO:3:

```
Met Ser Ser Lys Lys Leu Arg Arg Val Gly Leu Ser Pro Glu Leu Cys
  1               5                  10                  15

Asp Arg Leu Ser Arg Tyr Leu Ile Val Asn Cys Gln His Phe Leu Ser
             20                  25                  30

Leu Ser Pro Leu Glu Leu Met Lys Val Thr Gly Leu Ser Tyr Arg Gly
         35                  40                  45

Val His Glu Leu Leu His Thr Val Ser Lys Ala Cys Ala Pro Gln Met
     50                  55                  60

Gln Thr Ala Tyr Glu Leu Lys Thr Arg Arg Ser Ala His Leu Ser Pro
 65                  70                  75                  80

Ala Phe Leu Ser Thr Thr Leu Cys Ala Leu Asp Glu Ala Leu His Gly
                 85                  90                  95

Gly Val Pro Cys Gly Ser Leu Thr Glu Ile Thr Gly Pro Pro Gly Cys
             100                 105                 110

Gly Lys Thr Gln Phe Cys Ile Met Met Ser Val Leu Ala Thr Leu Pro
         115                 120                 125

Thr Ser Leu Gly Gly Leu Glu Gly Ala Val Val Tyr Ile Asp Thr Glu
     130                 135                 140

Ser Ala Phe Thr Ala Glu Arg Leu Val Glu Ile Ala Glu Ser Arg Phe
145                 150                 155                 160

Pro Gln Tyr Phe Asn Thr Glu Glu Lys Leu Leu Leu Thr Ser Ser Arg
                 165                 170                 175

Val His Leu Cys Arg Glu Leu Thr Cys Glu Gly Leu Leu Gln Arg Leu
             180                 185                 190

Glu Ser Leu Glu Glu Glu Ile Ile Ser Lys Gly Val Lys Leu Val Ile
         195                 200                 205

Val Asp Ser Ile Ala Ser Val Val Arg Lys Glu Phe Asp Pro Lys Leu
210                 215                 220

Gln Gly Asn Ile Lys Glu Arg Asn Lys Phe Leu Gly Lys Gly Ala Ser
225                 230                 235                 240

Leu Leu Lys Tyr Leu Ala Gly Glu Phe Ser Ile Pro Val Ile Leu Thr
                 245                 250                 255

Asn Gln Ile Thr Thr His Leu Ser Gly Ala Leu Pro Ser Gln Ala Asp
             260                 265                 270

Leu Val Ser Pro Ala Asp Asp Leu Ser Leu Ser Glu Gly Thr Ser Gly
         275                 280                 285

Ser Ser Cys Leu Val Ala Ala Leu Gly Asn Thr Trp Gly His Cys Val
     290                 295                 300

Asn Thr Arg Leu Ile Leu Gln Tyr Leu Asp Ser Glu Arg Arg Gln Ile
305                 310                 315                 320

Leu Ile Ala Lys Ser Pro Leu Ala Ala Phe Thr Ser Phe Val Tyr Thr
                 325                 330                 335

Ile Lys Gly Glu Gly Leu Val Leu Gln Gly His Glu Arg Pro
             340                 345                 350
```

(2) INFORMATION FOR SEQ ID NO:4:

(i) SEQUENCE CHARACTERISTICS:
        (A) LENGTH: 1525 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
GGGAGCCCTG GAAACATGAG CAGCAAGAAA CTAAGACGAG TGGGTTTATC TCCAGAGCTG      60

TGTGACCGTT TAAGCAGATA CCTGATTGTT AACTGTCAGC ACTTTTTAAG TCTCTCCCCA     120

CTAGAACTTA TGAAAGTGAC TGGCCTGAGT TACAGAGGTG TCCACGAGCT TCTTCATACA     180

GTAAGCAAGG CCTGTGCCCC GCAGATGCAA ACGGCTTATG AGTTAAAGAC ACGAAGGTCT     240

GCACATCTCT CACCGGCATT CCTGTCTACT ACCCTGTGCG CCTTGGATGA AGCATTGCAC     300

GGTGGTGTGC CTTGTGGATC TCTCACAGAG ATTACAGGTC CACCAGGTTG CGGAAAAACT     360

CAGTTTTGCA TAATGATGAG TGTCTTAGCT ACATTACCTA CCAGCCTGGG AGGATTAGAA     420

GGGGCTGTGG TCTACATCGA CACAGAGTCT GCATTTACTG CTGAGAGACT GGTTGAGATT     480

GCGGAATCTC GTTTTCCACA ATATTTTAAC ACTGAGGAAA AATTGCTTCT GACCAGCAGT     540

AGAGTTCATC TTTGCCGAGA GCTCACCTGT GAGGGGCTTC TACAAAGGCT TGAGTCTTTG     600

GAGGAAGAGA TCATTTCGAA AGGAGTTAAG CTTGTGATTG TTGACTCCAT TGCTTCTGTG     660

GTCAGAAAGG AGTTTGACCC GAAGCTTCAA GGCAACATCA AGAAAGGAA CAAGTTCTTG      720

GGCAAAGGAG CGTCCTTACT GAAGTACCTG GCAGGGGAGT TTTCAATCCC AGTTATCTTG     780

ACGAATCAAA TTACGACCCA TCTGAGTGGA GCCCTCCCTT CTCAAGCAGA CCTGGTGTCT     840

CCAGCTGATG ATTTGTCCCT GTCTGAAGGC ACTTCTGGAT CCAGCTGTTT GGTAGCTGCA     900

CTAGGAAACA CATGGGGTCA CTGTGTGAAC ACCCGGCTGA TTCTCCAGTA CCTTGATTCA     960

GAGAGAAGGC AGATTCTCAT TGCCAAGTCT CCTCTGGCTG CCTTCACCTC CTTTGTCTAC    1020

ACCATCAAGG GGGAAGGCCT GGTTCTTCAA GGCCACGAAA GACCATAGGG ATACTGTGAC    1080

CTTTGTCTAG TGCTGATTGC ATGTGACTCA TGAAATGAAA CAGGACTGCG CTGCTTGGAA    1140

AAAGGAAACG GAAGCCAACA TAATGAGGAT TAATTGGTTG GTTGCTGTTG AGGTGGTAAC    1200

AGTGATTTCA GACCCGGAAG GTGAAGATGA AGAAGCCTTT ATCCAGTCTC TGGATGCAGA    1260

GGCTAGGGGC TCCACCACCG TGGGATGTCA GCGGCCATCG TAATAATTTG CACTTACACA    1320

AGCACCTTTC AGCCATGCCC CTCAAAGTGG TTCAGCCACA TTAATTAATT AAAGCCCACA    1380

ATCCCCTAG GGAGAGCAGG AGGGGGACTA ACAAGATTTG TAATTACAGA AGGGAAAATT     1440

TCCGAATAAA GTATTGTTCC GCCAAAAAAA AAAAAAAAA AAAAAAAAA AAAAAAAAA       1500

AAAAAAAAAA AAAAAAAAAA AAAAA                                         1525
```

(2) INFORMATION FOR SEQ ID NO:5:

(i) SEQUENCE CHARACTERISTICS:
        (A) LENGTH: 1699 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:5:

```
CGACGGCCCG GGCTGGTATT ATAGCAGGTA TCACTTGGTT TTCTACTGGG GGAAACAAGT      60

CATTGCTAAC AAATTCCCAT GGGAGAGAAA TGAGGAGGAT GTATTTTGT TTGTGAGAGG      120

TGTGTATGTA TGTATATTGT GTGTGCGTGT GTGTGTGTGT GAGAGAGAGA GATTGATTCA     180

GTCTGATTCA GAGAATTTAG GTGTTAAATA GAAATTTGGG CCATGGTATT GGAAATAAAC     240

AAATATATAC ATTCTCAGTA TACATATATT TTCATTCCAA AATGTTACTT CTTTTCTGAT     300

AACTATATTG CTTTATTCCC TTGGATCCAT GAAGAGTTCC TGTTTCAGTT CGTTCCAGAG     360

GATACTTCTT TACCATCTCA ATGAGATATA CAGCTTCTCC TTTGTATGCA TTAAGAGACT     420
```

```
CACAGTAATT CTTTTTTAGC TCTGTGAAGA TAAATCTTTC ATGAGCCTCA TTTACCCCTA    480

GCAAAGTACA ATAGTGAAAT TTAACTGCAT GTGAGAATAT AAGCAGCTAG TGTAATAAAG    540

AACATTTTGG GCCAGGTCTG ATCGCTCATG CCTGTAATCC AGCACTTTA GGAGGTCAAG     600

GCGAGAGGAT CACTTGAGCC CAGGAGTTCG AGACCAGCTT GGGCAACATG GCAAAACCCT    660

GTCTCTACAA AAAATACAAA AATTGGGCAG GCATGGTGTC GACCCAGTCT CTACAAAAAA    720

TACAAAAATT AGCCAGACAT GGTGGTGCAC GCTTGTGGTC CCAGCTACTT GGGAGGCTGA    780

GGTAGGAGGA TTGCTTGAGC CCAGGAGGGG GAGGTTGCAG TGAGCTGAGA TCGAGCCACT    840

GCACTCCAGC TGGGGTGACA GAGCCAGACC TGTCTCGCTC TCTCTCTCTC TCTATATATA    900

TATATTTAAA AAGAACATTT TAATACTGCA GTGATAAAAT CTCATTTGAT TCAGAAGGTG    960

TGCTCTGACT CCTAGAAAAA GGAAGAGTCA AATATGATTA TGGACTTGCA GTAGAGTGTA   1020

ATGGTTAAGA GGATAGGTTT CAGAATTAGA CTGCCTGGAT TCAAATTCTG GATCAGTTAT   1080

TTATGGTTTC TGGTGACAAT GGACTAGCTA ACTTTCCAG GCTTTAGTTT TCTCATATGT    1140

AAAAAAGGGG CCAATAATCT ACTTTCCTTC TAGGGCTATT GAGAAGATTA AATGTGATAA   1200

TTTAGATAAG TTTTGGAACA GTGCCTGGTA TGTGGTAGGT GCTCCATAAA TATACCTATT   1260

GCCGTTACAG TGCAATGTAA ATTGTTACAG TGCAATAGAC TTTCTAGTAG TTCTGTTTGG   1320

AAATATGCCT TGAAAGTTAA TTACATTTCC AAATAAAATT TATACATGCA TTGGAACATT   1380

TTAAGATGCT CTACAAATGT GAAGTGGTAC TATATTCATG TAGTAAATAT CAATTAATTG   1440

TGTGAAATTA TATTTGAGGT TGCCTTGTAG ATTTTCTATG TGCCTGTTTG ACGAACAATT   1500

GTCCCTCCTA TTTAAAACAT TTAAAAAGGT TCTATAGCAT TCCTTTATCA GTAATATTTT   1560

TAACACAATA TGTTTCATTT TGCATATGGA GAAACTTGAG GAATTTTTAA TTTTGTTTTG   1620

GATAGCCTAT TCACTATCAC TTATGTTATA TTCTGTTGTT TTTTTCATGG TTCTTCTTTT   1680

CTTTGCTGGA TCTGGAGGC                                                1699

(2) INFORMATION FOR SEQ ID NO:6:

(i) SEQUENCE CHARACTERISTICS:
        (A) LENGTH: 2147 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:6:

TATCTCAGTA GCACGTGCAC ATAGCAACTA CAATACCTGT CACATAAATG TAGTTACTTG     60

AATATATGTC TCTTCATTCT TCAATTGTAA GTATGCAAAA GGGAGGACAT AAGCTTAGCA    120

TAGCATGTGC TTAATATTGG TGAAAGAAAC AAATGAATAG AGAATGTTAT ATTTGGAGAG    180

TTTATATTAT ATTTGGGAGA GTAGGGAAAA AACTTGAAGC CATAAGCAGA ATCGAGGGCA    240

AGTAGTGAGA GTGGTACTGT TAAATCAGAG TGATTATTGC TAAGGTCTTT GTAATTTGGG    300

GTTGTAGGTG TTTTTTGTTT TTGTTGTTTG AGGGTCTGAA TTTATTCGTT ATATGATGTT    360

ATTGCCTGGA ACTACCTTAT CTGAGAAGCA GTAGGCAATA GAGTAGCGTA TAAATGTTGG    420

TAAATTTTCT CTTAAGGAAA CAAATTATCC TTACAAAATT CCAACTGAAA GAAATAAAGA    480

GAATGTATCT TGGTTTTGTG TGGAGAGAGG GAAGTAGAAG ATGGGGGATG AAGAGAGAGA    540

GGAGGGTTAT TTATTGGGCT ATATATAGTG TTGGTAGTAG GAATCTTAAT TCTTGTGTGT    600

AGTTTTGTTC TTTTGTGTAT AGTTATTGAT TATTACTTTA TTCCATGGGA ATAATGAGTT    660
```

```
CCTATTATTT CTGGAGGATA TTTTGCCATT TCGATGAGAC ACACAGCCTC TTCTTTGCTA    720

TGCAATATTA CGAGATTACA ACAGTTCTAA CTCCCTGAAG ACAAATACTT CATGAGTCTC    780

ATTAGCTATC TAAGCTATAG GAAGAGCAGA ATTTAATTCT ACATGGAAAC AGTAAGAAGC    840

TAGTATAATG AAGAATTTTA TTGATATCAC TTGATTGAAA TTTGTTCTGA CTCTTTAGAA    900

AAAGCAAGGG TGAAATAAGA TTTGTGATTC TACAGTAGTA ATGGGTAAGA GGATAGGTCT    960

CAGGACAAAC TGCCTAATGA AACCCTAAAT CTGTTATTTA TTTATTTTCT GATGACAGTG   1020

GGATAACTGA CATTTACACA TTAGCTTTCT CATATGTAAA AAAGAAATTT TATTTTTATT   1080

ATAGTCTGTC AAGGAATATT AAATATAAGG TTTTGGAGCA TGGTTGATAT TTAGCAGATG   1140

TCTGTTCATT CTTGATCAGT ATAGAGTTGC CACTTGGAAA ATGCATCTTG AAGATTACAT   1200

AACCAGACAA AATTTGTTAG TAACACTCAG TGGTCTTAAG ATGTTATAAG TGACGGGCTA   1260

GTCGTGGTAA TCAACTTGAT ACCTTGACCC TCAGGAGAAG AGGGATTGTC TCCATCGGAT   1320

GGGCCTGTGA GCATATCTGT GGGGACGTTT TCTTGGACT GCCTAGTTGA TGGAAAAGGG    1380

CTTGGCTCAG TGTCAGTGGT CCTTCTTATG GTGAGCAAGC TGGGGGAAGC GTTGCAGTAA   1440

GCAGTAGTCC TTTGTGGTCT CAGCTTCCTT TTCTTCTCTC TTCTTTCTTT CTTTCTTTCT   1500

TTCTTTCTTT CTTTCTTTCT TTCTTCCTTC CTTCCTTCCT TTTCTCTCTT TCTTTCTTTA   1560

GTTCCGTTCG TTTGTTCATT CGTTCGTTTT TCGAGACAGG GTTTTTCTGT ATAGCCCTGG   1620

CTGTCCTGGA ACTCACTTTG TAGACCAGGC TGTCCTCGAA CTCAGAAATC CGCCTGCCTC   1680

TGCCTCCCTG TGAGTGCTGG AATTAAAGGC ATGCGCCACC CCGCCCGGCT TCTCAGCTTC   1740

CATTTCTGTT CAAGCTCTTG CCTTCAGCTC CTGCCTTGGC TTTCTGAGAC AAAGGCATAT   1800

AATCTGTAAG CCAAATCAAA CTTTTCTTCT CAACTTGCTT TTGGCCAGTG TTTTATTACA   1860

GCGACTAAAG GCAAACTAGA CTACTATGTA AATGGGAAGC ACTGTTAAAG TCAAGTAATA   1920

GCAAAAGATT ACATGGCCTG GATTTTTTGA GGTTGCTTAC TTTCTCTGTG TACCCGGTTG   1980

TAAGTGTCTT TCCTACTTTT TTTATTAGCA TTTTTTTTCC ATGTTTTGCT TTGCACATAG   2040

AGAAGTTTGA AGCACTTTAT TTTGTAGGGT GTTTTGTATA ATCTGTCCAC CATCATTTTT   2100

ATTGTTTTCT TATGTTTTTT CAAGATTTCT TTGGGAGCCC TGGAAAC                2147

(2) INFORMATION FOR SEQ ID NO:7:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Gly Lys Thr Gln Met
 1               5

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:8:

CAGACGGTCA CACAGCTCTT GTGATAA                                         27
```

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:9:

ACCCACTCGT TTTAGTTTCT TGCTAC                                    26

(2) INFORMATION FOR SEQ ID NO:10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:10:

TAGAGAGAGA GAGAGAGCGA GACAG                                     25

(2) INFORMATION FOR SEQ ID NO:11:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:11:

GTCGACCACG CGTGCCCTAT AG                                          22

(2) INFORMATION FOR SEQ ID NO:12:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:12:

TCACTGCATC TGGAAGCAC                                                19

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:13:

CTAACTAAAT GGCGAGCATT GAG                                     23

(2) INFORMATION FOR SEQ ID NO:14:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:14:

GAGCTCGAGG GTACCCATGG GTAGCAAGAA AC                            32

```
(2) INFORMATION FOR SEQ ID NO:15:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:15:

CGAGGAAGCA GT                                                           12

(2) INFORMATION FOR SEQ ID NO:16:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:16:

CGAGGAAGAA AA                                                           12

(2) INFORMATION FOR SEQ ID NO:17:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:17:

GGAGGCATTA AA                                                           12

(2) INFORMATION FOR SEQ ID NO:18:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:18:

GGTGGCGAAA TT                                                           12

(2) INFORMATION FOR SEQ ID NO:19:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:19:

CGTTACCCTA T                                                            11

(2) INFORMATION FOR SEQ ID NO:20:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:20:

SGWGGMRRNA NA                                                           12
```

(2) INFORMATION FOR SEQ ID NO:21:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 5...5
        (D) OTHER INFORMATION: N can be any nucleotide (xi) SEQUENCE DESCRIPTION: SEQ ID NO:21:

CGTTNCCCTA T                                                          11

(2) INFORMATION FOR SEQ ID NO:22:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 5...5
        (D) OTHER INFORMATION: N can be any nucleotide (xi) SEQUENCE DESCRIPTION: SEQ ID NO:22:

CCTANCCCTA A                                                          11

(2) INFORMATION FOR SEQ ID NO:23:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO :23:

CGTTACCCTA T                                                          11

(2) INFORMATION FOR SEQ ID NO:24:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO:24:

CGTTACCCAA T                                                          11

(2) INFORMATION FOR SEQ ID NO:25:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO:25:

CGGTTGCCAT G                                                          11

(2) INFORMATION FOR SEQ ID NO:26:

(i) SEQUENCE CHARACTERISTICS:

(A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO:26:

CGTTACCCTA T                                                                11

(2) INFORMATION FOR SEQ ID NO:27:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:27:

GTAGGTCGAA                                                                  10

(2) INFORMATION FOR SEQ ID NO:28:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:28:

CGAGGAAGCA                                                                  10

(2) INFORMATION FOR SEQ ID NO:29:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:29:

CGAGGAAGAA                                                                  10

(2) INFORMATION FOR SEQ ID NO:30:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:30:

CGTGGAGGCA                                                                  10

(2) INFORMATION FOR SEQ ID NO:31:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:31:

CGTGGTGGGA                                                                  10

(2) INFORMATION FOR SEQ ID NO:32:

(i) SEQUENCE CHARACTERISTICS:
        (A) LENGTH: 10 base pairs (B) TYPE: nucleic acid
       (C) STRANDEDNESS: single
       (D) TOPOLOGY: linear (xi) SEQUENCE DESCRIPTION: SEQ ID NO:32:

CGAGGATGAC                                                              10

(2) INFORMATION FOR SEQ ID NO:33:

(i) SEQUENCE CHARACTERISTICS:
       (A) LENGTH: 10 base pairs
       (B) TYPE: nucleic acid
       (C) STRANDEDNESS: single
       (D) TOPOLOGY: linear (xi) SEQUENCE DESCRIPTION: SEQ ID NO:33:

CGTGGTTGAT                                                              10

(2) INFORMATION FOR SEQ ID NO:34:

(i) SEQUENCE CHARACTERISTICS:
       (A) LENGTH: 10 base pairs
       (B) TYPE: nucleic acid
       (C) STRANDEDNESS: single
       (D) TOPOLOGY: linear (xi) SEQUENCE DESCRIPTION: SEQ ID NO:34:

CGAGGTCGCA                                                              10

(2) INFORMATION FOR SEQ ID NO:35:

(i) SEQUENCE CHARACTERISTICS:
       (A) LENGTH: 10 base pairs
       (B) TYPE: nucleic acid
       (C) STRANDEDNESS: single
       (D) TOPOLOGY: linear (xi) SEQUENCE DESCRIPTION: SEQ ID NO:35:

CTAGGTAGCA                                                              10

(2) INFORMATION FOR SEQ ID NO:36:

(i) SEQUENCE CHARACTERISTICS:
       (A) LENGTH: 10 base pairs
       (B) TYPE: nucleic acid
       (C) STRANDEDNESS: single
       (D) TOPOLOGY: linear (xi) SEQUENCE DESCRIPTION: SEQ ID NO:36:

GTAGGTGTTA                                                              10

(2) INFORMATION FOR SEQ ID NO:37:

(i) SEQUENCE CHARACTERISTICS:
       (A) LENGTH: 10 base pairs
       (B) TYPE: nucleic acid
       (C) STRANDEDNESS: single
       (D) TOPOLOGY: linear (xi) SEQUENCE DESCRIPTION: SEQ ID NO:37:

CTAGGTAACA                                                              10

(2) INFORMATION FOR SEQ ID NO:38:

(i) SEQUENCE CHARACTERISTICS:
       (A) LENGTH: 10 base pairs
       (B) TYPE: nucleic acid

```
        (C) STRANDEDNESS: single
        (D) TOPOLOGY: linear (xi) SEQUENCE DESCRIPTION: SEQ ID NO:38:

CATGGTTGCC                                                              10

(2) INFORMATION FOR SEQ ID NO:39:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:39:

CGWGGWNGMM                                                              10
```

US 6,410,226 B1

MAMMALIAN AND HUMAN REC2

This application claims benefit of the priority of U.S. provisional application Serial No. 60/025,929, filed Sep. 11, 1996.

1. FIELD OF THE INVENTION

The present invention concerns the field of molecular genetics and medicine. Particularly, it concerns genes encoding a protein that is involved in homologous recombination and the repair of damaged genomic DNA in mammalian cells. Specifically the invention concerns the gene encoding a mammalian ATP-dependent homologous pairing protein; methods of using the gene to effect gene therapy; methods of using the gene and fragments of the gene to classify a mammalian tissue for medical purposes; and transgenic mice having had one or both alleles of the gene made inoperative. More specifically, the gene of the present invention is the human and murine homologs of the gene termed REC2 previously isolated from the fungus *Ustilago maydis*.

2. BACKGROUND OF THE INVENTION

During the life of every organism the DNA of its cells is constantly subjected to chemical and physical events that cause alterations in its structure, i.e., potential mutations. These potential mutations are recognized by DNA repair enzymes found in the cell because of the mismatch between the strands of the DNA. To prevent the deleterious effects that would occur if these potential mutations became fixed, all organisms have a variety of mechanisms to repair DNA mismatches. In addition, higher animals have evolved mechanisms whereby cells having highly damaged DNA, undergo a process of programmed death ("apoptosis").

The association between defects in the DNA mismatch repair and apoptosis inducing pathways and the development, progression and response to treatment of oncologic disease is widely recognized, if incompletely understood, by medical scientists. Chung, D. C. & Rustgi, A. K., 1995, Gastroenterology 109:1685–99; Lowe, S. W., et al., 1994, Science 266:807–10. Therefore, there is a continuing need to identify and clone the genes that encode proteins involved in DNA repair and DNA mismatch monitoring.

Studies with bacteria, fungi and yeast have identified three genetically defined groups of genes involved in mismatch repair processes. The groups are termed, respectively, excision repair group, the error prone repair group and recombination repair group. Mutants in a gene of each group results in a characteristic phenotype. Mutants in the recombination repair group in yeast result in a phenotype having extreme sensitivity to ionizing radiation, a sporulation deficiency, and decreased or absent mitotic recombination. Petes, T. D., et al., 1991, in Broach, J. R., et al., eds., The Molecular Biology of the Yeast Saccharomyces, pp. 407–522 (Cold Spring Harbor Press, 1991).

Several phylogenetically related genes have been identified in the recombination repair group: recA, in *E. Coli*, Radding, C. M., 1989, Biochim. Biophys. Acta 1008:131–145; RAD51 in *S. cerevisiae*, Shinohara, A., 1992, Cell 69:457–470, Aboussekhra, A. R., et al., 1992, Mol. Cell. Biol. 12:3224–3234, Basile, G., et al., 1992, Mol. Cell. Biol. 12:3235–3246; RAD57 in *S. cerevisiae*, Gene 105:139–140; REC2 in *U. maydis*, Bauchwitz, R., & Holloman, W. K., 1990, Gene 96:285–288, Rubin, B. P., et al., 1994, Mol. Cell. Biol. 14:6287–6296. A third *S. cerevisiae* gene DMC1, is related to recA, although mutants of DMC1 show defects in cell-cycle progression, recombination and meiosis, but not in recombination repair.

The phenotype of REC2 defective *U. maydis* mutants is characterized by extreme sensitivity to ionizing radiation, defective mitotic recombination and interplasmid recombination, and an inability to complete meiosis. Holliday, R., 1967, Mutational Research 4:275–288. UmREC2, the REC2 gene product of *U. maydis*, has been extensively studied. It is a 781 amino acid ATPase that, in the presence of ATP, catalyzes the pairing of homologous DNA strands in a wide variety of circumstances, e.g., UmREC2 catalyzes the formation of duplex DNA from denatured strands, strand exchange between duplex and single stranded homologous DNA and the formation of a nuclease resistant complex between identical strands. Kmiec, E. B., et al., 1994, Mol. Cell. Biol. 14:7163–7172. UmREC2 is unique in that it is the only eukaryotic ATPase that forms homolog pairs, an activity it shares with the *E. coli* enzyme recA.

U.S. Pat. No. 5,780,296 filed Jan. 17, 1995, by W. K. Holloman and E. B. Kmiec discloses REC2 from *U. maydis*, methods of producing recombinant UmREC2 and methods of its use. Prior to the date of the present invention a fragment of human REC2 cDNA was available from the IMAGE consortium, Lawrence Livermore National Laboratories, as plasmid p153195. Approximately 400 bp of the sequence of p153195 had been made publicly available on dbEST database.

The scientific publication entitled: Isolation of Human and Mouse Genes Based on Homology to REC2, July 1997, Proc. Natl. Acad. Sci. 94, 7417–7422 by Michael C. Rice et al., discloses the sequences of murine and human Rec2, of the human REC2 cDNA. and discloses that irradiation increases the level of hsREC2 transcripts in primary human foreskin fibroblasts.

3. SUMMARY OF THE INVENTION

The invention provides nucleic acids encoding mammalian ATP-dependent homologous pairing proteins (a "mammalian recombinase") particularly, the human and murine ATP-dependent homologous pairing protein (hsREC2 and muREC2, respectively). The invention additionally provides DNA clones containing a copy of the mRNA encoding a mammalian recombinase (an "mREC cDNA") and DNA clones containing a copy of the genomic DNA containing an mREC gene or fragments thereof. In further embodiments, the invention concerns a nucleic acid comprising an mREC cDNA linked to a heterologous promoter, i.e., a promoter other than a mammalian recombinase promoter, so that a mammalian recombinase can be expressed or over-expressed in insect and mammalian cells and in bacteria. In one embodiment, the heterologous promoter is the polyhedrin promoter from the baculovirus *Autographica californica* and the invention provides for an isolated and purified mammalian recombinase, particularly isolated and purified hsREC2.

The invention provides several utilities of said nucleic acids and isolated and purified proteins. In the area of gene therapy and the construction of transgenic animals, the invention provides a method of enhancing homologous recombination between an exogenous nucleic acid and the genome of a cell by introducing a plasmid that expresses an mammalian recombinase into the cell, which method can be used to repair a genetic defect and thereby cure a genetic disease. Alternatively, for the construction of transgenic animals the invention provides a method of enhancing homologous recombination between an exogenous nucleic acid and the genome of a cell by introducing purified mammalian recombinase into the cell. Alternatively, the invention provides for the construction of a transgenic animal, such as a mouse, having a transgenic mammalian recombinase gene operably linked to a strong promoter so that the recombinase is over expressed in some or all tissues. Such transgenic animals are highly adapted to undergo homologous recombination.

The invention additionally provides two methods of classifying a sample of human tissue for diagnosis and prognosis: by determining whether the cells of the sample contains two, one or no copies of hsREC2; and by determining whether the copies of hsREC2 that said cells contain are mutated. For the purpose of diagnosis and classification of tissue samples the invention, firstly, provides paired oligonucleotides that are suitable for the PCR amplification of fragments of hsREC2 and, secondly, identifies a microsatellite DNA sequence, D14S258, that is closely linked to hsREC2.

The invention further provides a transgenic mouse having one or both alleles of muREC2 interrupted and thereby inactivated. The resultant transgenic animals, termed heterozygous and homozygous REC2-knock out mice, respectively, are susceptible to tumorigenesis by chemical carcinogens. REC2-knock-out mice can be used to determine whether their is a significant risk of carcinogenesis associated with a chemical or a process of interest. The reduced level or absence of muREC2 makes REC2-knock-out mice a more sensitive test animal than wild-type.

The invention further provies a method of sensitizing target cells to DNA damage, such as from γ- or UV irradiation or from cytotoxic agents commonly used in oncologic therapy, which comprises causing the expression of high levels of recombinase in the target cell. The expression of such levels causes the cells to more readily undergo apoptosis in response to DNA damage. The invention yet further provides the REC2 promoter a mammalian promoter that is induceable by irradiation or other DNA damaging agents.

4. BRIEF DESCRIPTION OF THE FIGURES

FIGS. 1A–1G.

FIGS. 1A and 1B show the derived amino acid sequence of hsREC2 (SEQ ID NO:1) and FIGS. 1C and 1D show the nucleic acid sequences of the hsREC2 cDNA coding strand (SEQ ID NO:2), respectively. FIGS. 1E and 1F show the derived amino acid sequence of muREC2 (SEQ ID NO:3) and FIG. 1G shows the nucleic acid sequences of the hsREC2 cDNA coding strand (SEQ ID NO:4), respectively.

FIGS. 2A–2D.

FIG. 2A is an annotated amino acid sequence of hsREC2. Specifically noted are the nuclear localization sequence ("NLS"), A Box and B Box motif sequences, DNA binding sequence and a src-type phosphorylation site ("P"). FIG. 2B is a cartoon of the annotated sequence, showing in particular the region 80–200 is most closely related to recA. FIGS. 2C–2D shows the sequence homology between hsREC2 and *Ustilago maydis* REC2. The region of greatest similarity, 43% homology, is in bold.

FIG. 3.

Figure 3:
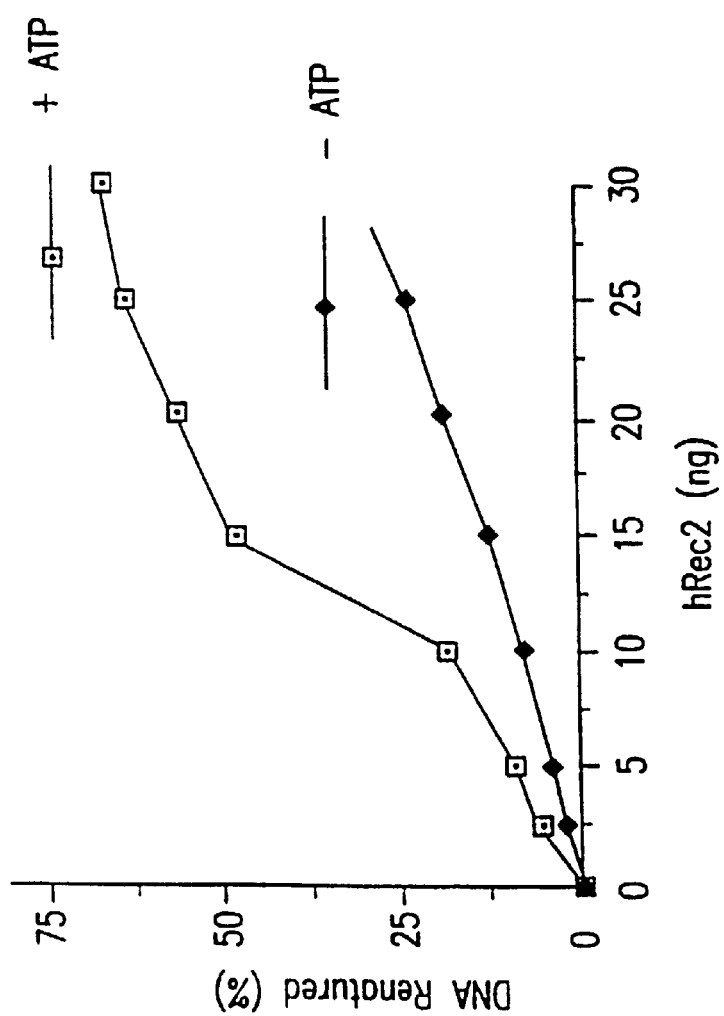

FIG. 3 shows the DNA reannealing as a function of added baculovirus-produced hexahistidylHsREC2.

FIG. 4.

Figure 4:

FIG. 4 is a gel shift assay showing that binding of a hsREC2-thioredoxin fusion protein to ssDNA is ATP or γ-SATP dependent.

FIGS. 5A–5B.

Figure 5A:
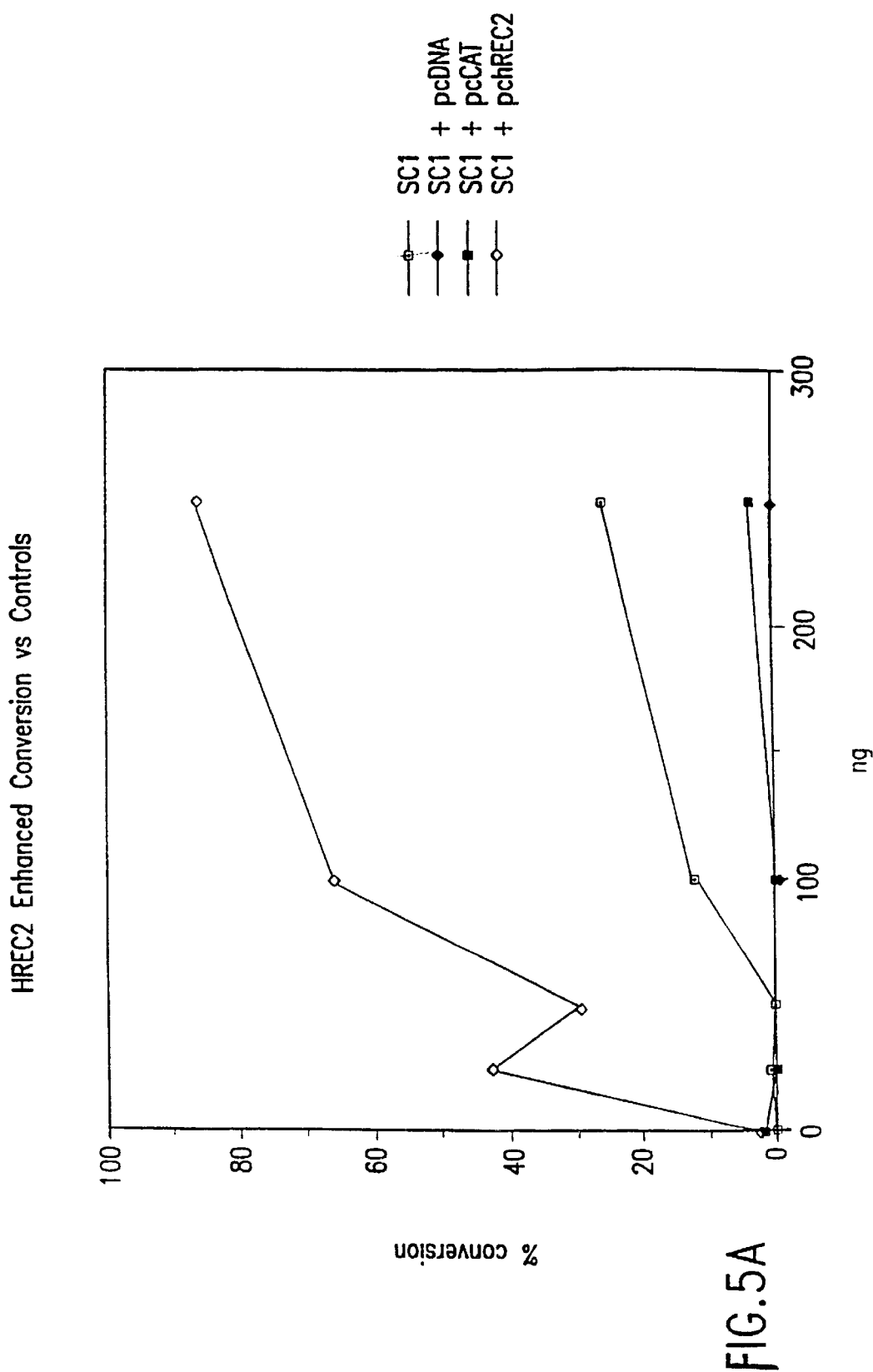
Figure 5B:
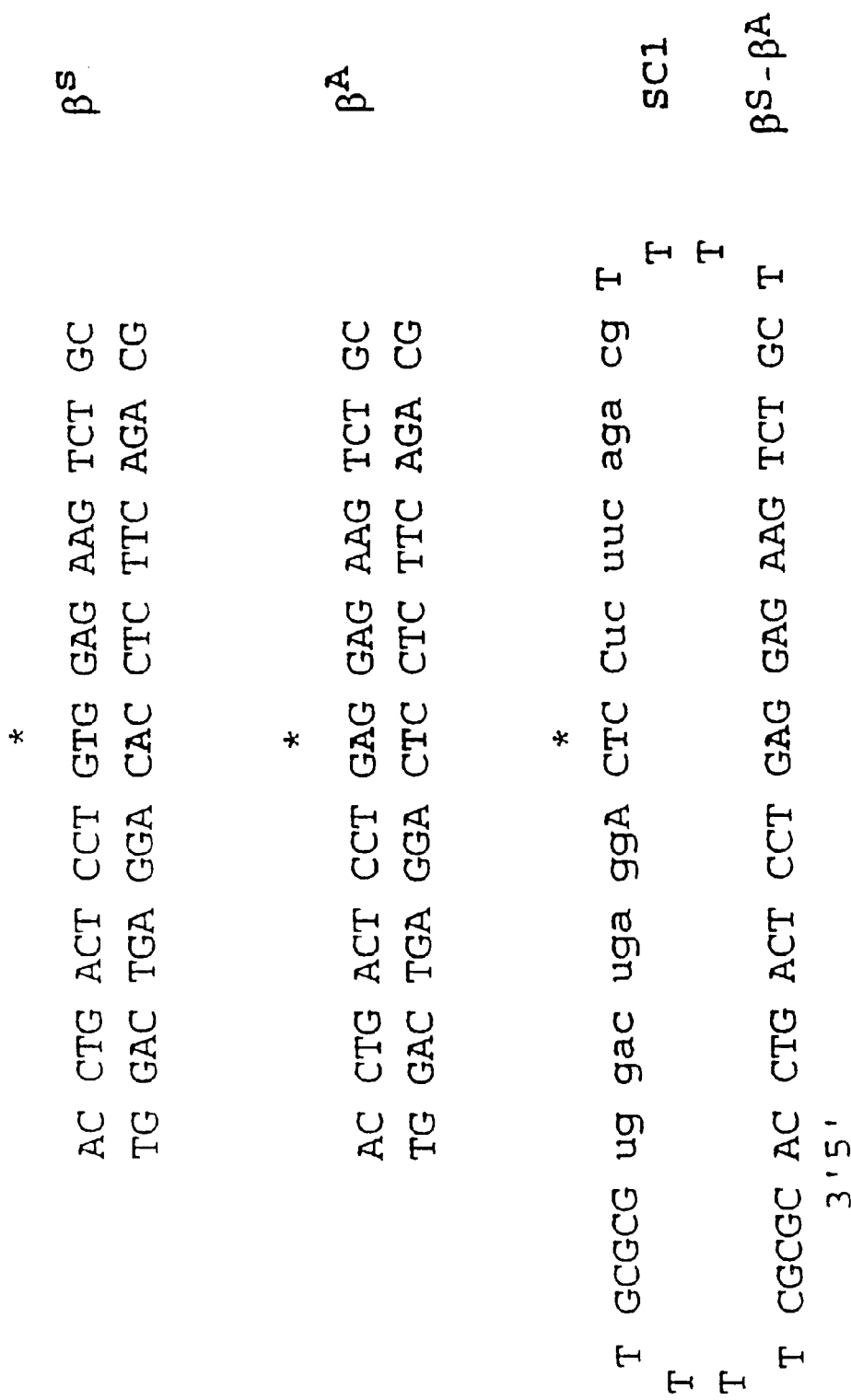

FIG. 5A shows the frequency of repair of the Sickle Cell Disease mutation, as a function of added $\beta^S \rightarrow \beta^A$ chimeric repair vector (SC1), in the β-globin genes in a population of EBV-transformed human lymphoblasts in the presence or absence of the hsREC2 expression vector pcHsREC2, pcDNA3 or pcCAT control plasmids or SC1 alone. FIG. 5B shows the sequences of SC1, $\beta^S$ and $\beta^A$ in the region of the Sickle Cell mutation. Lower case a, c, g, and u indicates 2'-OMe nucleotides.

FIG. 6.

Figure 6:
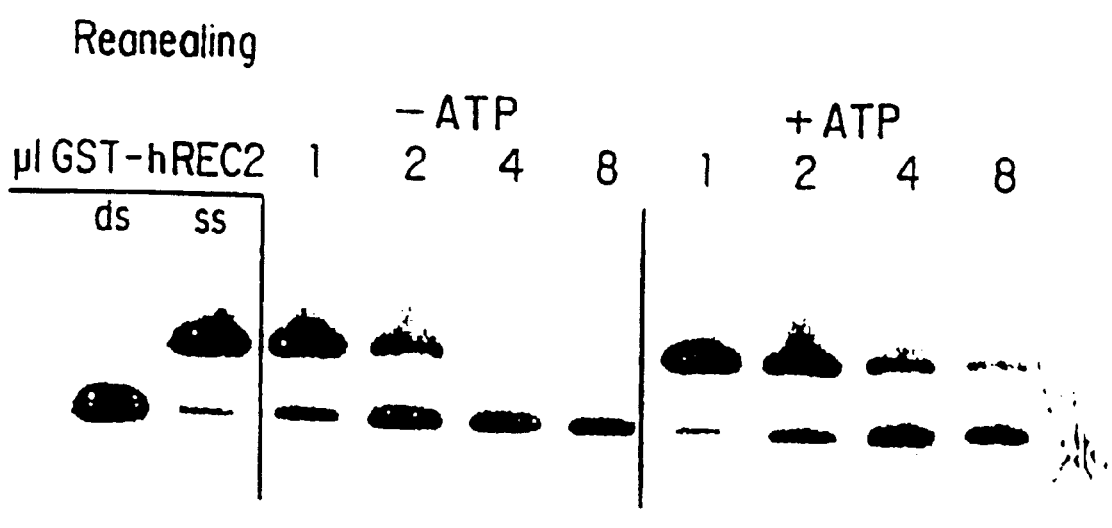
Figure 8A:
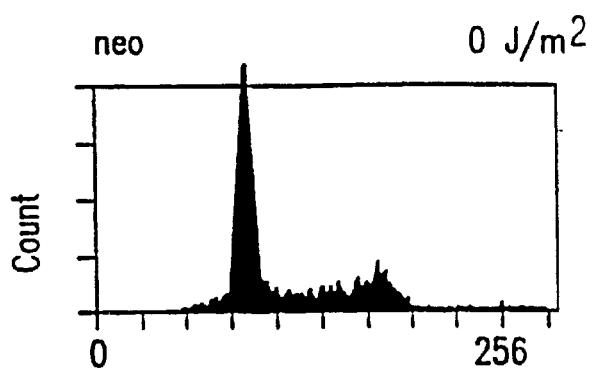
Figure 8B:
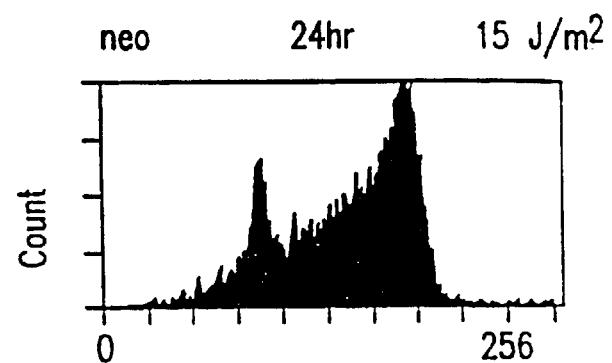
Figure 8C:
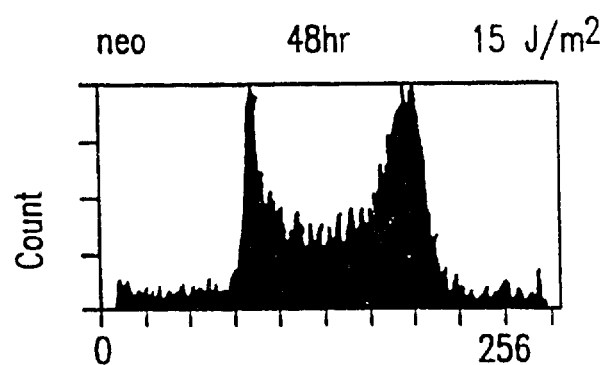
Figure 8D:
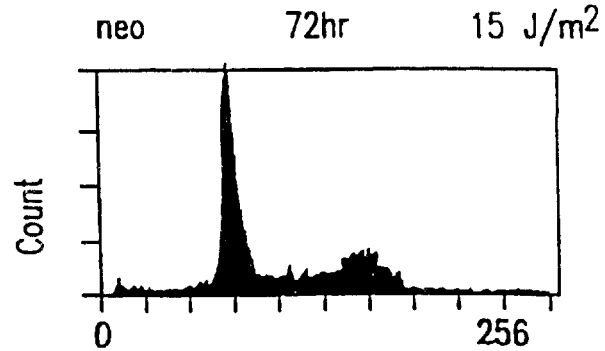
Figure 8E:
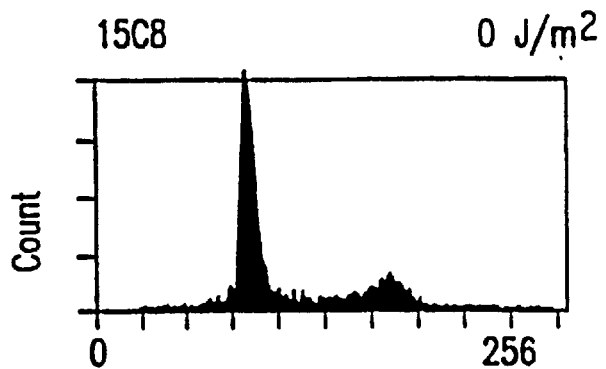
Figure 8F:
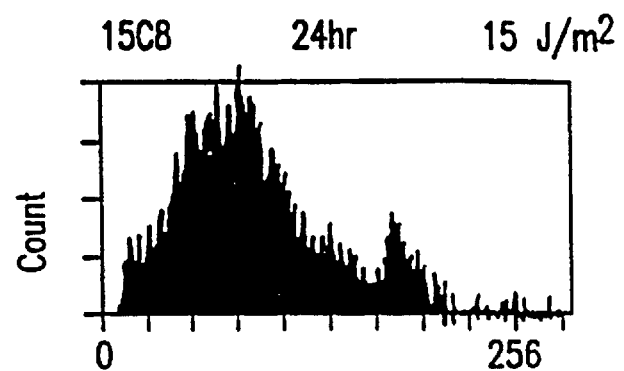
Figure 8G:
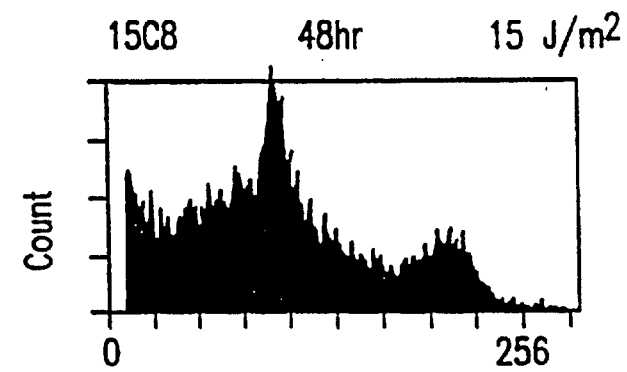
Figure 8H:
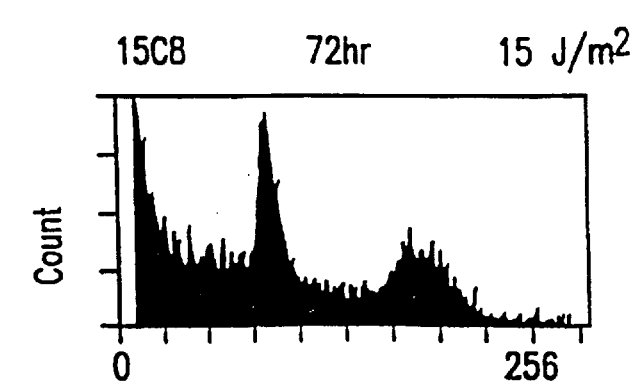

FIG. 6 shows the reannealing of a 123 nt DNA fragment is catalyzed by GST/REC2 fusion protein.

FIGS. 7A–7C and 7D–7F.

FIGS. 7A–7C and 7D–7F show the sequence of the hsREC2 and muREC2 promoters respectively. The locations of sequences homologous to the sequences of known cis-acting radiation responsive elements in yeast are underlined and the corresponding yeast gene is indicated.

FIGS. 8A–8H.

FIGS. 8A–8H show FACS histograms of Rnase treated, propidium iodide stained, CHO cells that have been transfected with either an hsREC2 expressing plasmid (15C8) or an irrelevant control plasmid (Neo). The DNA content of the cells is displayed in the horizontal axis. The histograms are of unirradiated cells (8A, 8E) or of cells that are 24, 48 or 72 hours status post exposure to 15 J/m² UV irradiation (8B–8D, 8F–8H). The comparison shows that the expression of hsREC2 increases the fraction of irradiated cells having less than the diploid DNA content, which is indicative of apoptosis.

5. DETAILED DESCRIPTION OF THE INVENTION

As used herein, genes are italicized, e.g., hsREC2, while the corresponding protein is in normal typeface.

5.1 hsREC2 and the Structure of its Product hsREC2

The results of efforts to obtain hsREC2 cDNA by hybridization under non-stringent conditions with UmREC2 probes were unsatisfactory. Efforts were made to isolate a fragment of hsREC2 by PCR amplification using primers that encode pentapeptides based on the UmREC2 sequence. A mixture of four forward primers encoding residues 256–260 of UmREC2, GKTQM (SEQ ID NO:7), was constructed using inosine as the third base for the gly and thr codons and having a 5' noncoding GC dinucleotide, i.e., 5'-GC GGI AA(G/A) ACI CA(G/A) ATG-3'. A mixture of eight reverse primers complementary to the sequences that can encode residues 330–334 of UmREC2, YITSG, was synthesized, using inosine in the same way as the forward primers, i.e., 5'-CC ICC G(C/G)(T/A)¹ IGT IAT (A/G)TA-3'. The primers were used to amplify fragments of human genomic and cDNA libraries using the Expand™ system (Boehringer) coupled with two rounds of reamplification. After reamplification the fragments were cloned in pCRII (Invitrogen). Ten different mixtures of primers encoding a total of nine different pentapeptides were used and a total of about 60 fragments were sequenced. One 110 bp fragment from a human kidney cDNA library, hsr110, had statistically significant homology with UmREC2.

<sub>Only two of the four combinations are complementary to ser codons, however, they are complementary to the ser codons most often used in humans.</sub>

A computer search of the database dbEST was performed to find clones of cDNAs encoding proteins that have significant homologies with UmREC2 and hsr110. The plasmid p153195 was identified as having significant homology with UmREC2 and which contained hsr110. In one segment of 44 residues of UmREC2 and hsREC2, there was 43% homology between UmREC2 and hsREC2, i/e/, 19 of the 44 residues of each sequence were identical. Additionally, there were 8 conservative substitutions. This region of high homology corresponds to residues 84–127 of hsREC2 and residues 226–270 of UmREC2. See FIGS. 2C–2D. Residues 226–270 of UmREC2 is the portion of UmREC2 that is most highly conserved when compared to recA and related members of the recombination repair group; cf. Residues 40–95 of recA, 95–13 of DMC1, residues 100–144 of RAD51, and residues 160–204 of RAD51. See, e.g., FIG. 2, Rubin et al., 1994 *supra*.

That clone p153195 lacked the 5' end of hsREC2 was determined by the absence of an inframe start codon. The 5' end of hsREC2 cDNA was obtained by PCR amplification of a cDNA library using a forward primer from the cloning vector and nested reverse primers based on p153195. An over lap of about 100 bp was identified which contained a unique restriction site that was used to reconstruct the full length hsREC2 cDNA. The sequences of the reconstructed hsREC2 cDNA and the derived sequence of hsREC2 are given in FIGS. 1A–1D. The hsREC2 cDNA encodes a protein of 350 amino acids, SEQ ID NO: 1 of FIG. 1. The sequence of the hsREC and its complement are SEQ ID NO: 2 and No: 3, respectively. The 5' boundary of p153195 was about nt280 of SEQ ID NO: 2.

Comparisons of the hsREC2 sequence with the UmREC2 sequence reveals statistically significant, but distant homologies ($p=2.8 \times 10^{-5}$). A similar level of homology is found between hsREC2 and the yeast protein DMC1.

An expression vector containing the complete hsREC2 cDNA under control of a strong promoter, for example, the cytomegalovirus promoter (pcHsREC2), can be constructed for over-expression of hsREC2 in transferred eukaryotic cells. For the production of purified hsREC2 a vector suitable for the expression of the hsREC2 under control of the baculovirus polyhedrin promoter can be constructed. It is preferred to construct a vector that synthesizes a REC2 fusion protein consisting of a protein or peptide that aids in the purification of the product, such as a hexahistidyl peptide or glutathione S-transferase. FIGS. 1E–1F and 1G show the derived amino acid and nucleic acid sequences of the murine REC2 (muREC2) cDNA

5.2 Homologs of hsREC2

The present invention encompasses mammalian homologs of hsREC2. Nucleic acids encoding the REC2 from any mammalian species can be identified and isolated by techniques, routine to those skilled in the art, using the sequence information of FIGS. 1A–1D and/or the hsREC2 cDNA clone. Such routine techniques include use of the hsREC2 cDNA or fragments thereof to probe cDNA and genomic libraries from other mammalian species and use of the sequence data to construct primers for PCR amplification of fragments of mammalian REC2 cDNA. The cloning of hsREC2 and muREC2 genomic DNA (gDNA) is described below.

High levels of transcripts of hsREC2 can be found in heart and skeletal muscle, lung, pancreas, spleen and thymus, and placenta. Moderate or low levels of hsREC transcripts are found in liver, kidney, brain and testes. Thus, the source of mRNA to construct cDNA libraries for obtaining mammalian REC2 clones is not critical. The sequence of residues 83–127, which corresponds to amino acids 226–270 of UmREC2, is particularly highly conserved and is, therefore, useful in identifying mammalian REC2 homologs.

Mammalian homologs of hsREC2 can be identified by the presence of an amino acid sequence identity of greater than 80% and preferably greater than 90% compared to hsREC2 in the highly conserved portions of the gene, i.e., the portion homologous to residues 83–127 of hsREC2. In a preferred embodiment the mammalian recombinase gene shares greater than 80% sequence identity with hsREC2 gene within the about 130 bp segment that encodes the residues homologous with residues 83–127 of hsREC2. Such mammalian homologs of hsREC2 will also have the above-noted activities of catalyzing DNA reannealing, ATPase activity and ATP-dependent ssDNA binding activity.

As used herein, a protein having each of these three activities is termed an ATP-dependent homologous pairing protein (a "mammalian recombinase"). A mammalian recombinase having greater than an 80% sequence identity with hsREC2 is termed an "mREC2." Based on the extensive studies of bacterial and yeast homologous recombination proteins, those skilled in the art anticipate that all mammalian recombinases will have greater than 80% amino acid sequence identity with hsREC2, i.e., be an mREC2.

The invention further encompasses fusion proteins comprising a mammalian REC2 protein or fragment thereof, wherein the REC2 fragment displays at least one and preferably each of the three above-noted activities to substantially the same extent as the native REC2. Those skilled in the art appreciate that the recombinant production and purification of mammalian proteins in bacterial and insect cell based expression systems is facilitated by the construction of fusion proteins that contain the protein of interest and a second protein that stabilizes the resultant fusion protein and facilitates its purification. Non-limiting examples of fusion proteins include hexahistidyl, Glutathione-S-transferase and thioredoxin fused to the amino terminus of REC2.

In one embodiment, the invention is a composition containing an isolated and purified protein, which is an ATP-dependent homologous pairing protein, i.e., is an ATP-dependent catalyst of DNA reannealing, is an ATPase, and binds ssDNA in the presence of ATP or γ-SATP, and which protein comprises a polypeptide of at least 115 amino acids which is substantially identical to a polypeptide found in a mammalian ATP-dependent homologous pairing enzyme. More preferably the isolated and purified protein comprises a polypeptide that is substantially identical to residues 80–200 of hsREC2. In a further embodiment, the isolated and purified protein of the invention comprises the polypeptide which is residues 2–350 of SEQ ID NO:1. As used herein, substantially identical means identical or having at most one conservative substitution per 20 amino acids. As used herein a human protein is an isolated and purified human protein if the composition containing the protein is substantially free of all other normally intracellular human proteins but a defined set of individually identified human proteins; similarly an isolated and purified mammalian protein is free of all other normally intracellular mammalian proteins except for a defined set of individually identified mammalian proteins. As used herein, "a composition which comprises a defined protein substantially free of a named material" means that the weight of the named material in the composition is less than 5% of the weight of the protein in the composition.

The invention further provides an isolated and purified nucleic acid derived from a mammalian species, i.e., derived from a cDNA or gDNA clone, that encodes a protein or fusion protein, having a sequence, which comprises the sequence of a mammalian ATP-dependent homologous pairing protein or a substantially identical sequence. As used herein, an isolated and purified nucleic acid is a nucleic acid isolated and purified free of nucleic acids encoding other mammalian proteins or fragments thereof. As used herein, the sequence of a mammalian ATP-dependent homologous pairing protein means the sequence of a naturally occurring, i.e., wild-type ATP-dependent homologous pairing protein found in a mammal, or of any mutants of wild-type mammalian ATP-dependent homologous pairing protein. In preferred embodiments the nucleic acid of the invention encodes a protein that is greater than 80% sequence identical, or alternatively, more than 90% sequence identical to hsREC2. Those skilled in the art appreciate that the N-terminal and C-terminal one, two or three amino acids can be substituted or deleted without effect and, as used herein, are not considered a part of the sequence unless so specified. Those skilled in the art further appreciate that the insertion or deletion of one to four consecutive amino acids during the evolution of homologous proteins is common. Therefore, in the definition of sequence identity between proteins encompasses the introduction of as many as four, one to four residue gaps in one or both sequences to maximize identity.

The isolated and purified nucleic acids of the invention encompass not only cDNA and gDNA clones of mammalian genes encoding a mammalian ATP-dependent homologous pairing protein, but also nucleic acids derived from said cDNA and gDNA clones by site directed mutagenesis. By use of routine PCR techniques, those skilled in the art can make specific, predetermined changes in the sequence of a DNA. Site directed mutagenesis may be conducted by any method. The method of Ho, S. N., et al., GENE 77:51–59 (herewith incorporated by reference in its entirety), is suitable. According to the method of Ho, overlapping, mutated genome fragments are synthesized in two separate PCR reactions. Of the four primers are used in the two reactions, two are complementary to each other and introduce the desired mutation. The PCR reactions are performed so that the 3' end of the sense strand of one product is complementary to the 3' end of antisense strand of the other. The two PCR products are denatured, mixed and reannealed. The overlapping partial duplex molecules are then extended form a full length dsDNA, amplified in a third PCR reaction, the product isolated and inserted by conventional recombinant techniques into the parent gene. See, also, Liang, Q., et al., 1994, PCR Methods & Applic. 4:269–74; Weiner, M. P. & Costa, G. L., 1994, PCR Methods & Applic. 4:S131–136; Barrettino, D., et al., 1994, Nucleic Acids Research 22:541; Stemmer, W. P., et al., 1992, Biotechniques 13:214–220. By multiple applications of such techniques any desired modifications in the sequence of a cloned DNA can be introduced. Thus, the nucleic acids of the invention are not limited to isolated and purified nucleic acids having naturally occurring sequences, but also include nucleic acids encoding a ATP-dependent homologous pairing protein having substantially the same sequence as a naturally occurring mammalian recombinase.

The compositions of the invention further include compositions comprising not only mammalian recombinases isolated and purified free of mammalian proteins, but also compositions comprising any isolated and purified ATP-dependent homologous pairing protein having substantially the same sequence as a naturally occurring mammalian recombinase.

The hsREC2 sequence contains several sequences that have been identified with specific functions in other proteins. FIG. 2A shows the sequence of hsREC2 and indicates the locations of nuclear localization sequence, four sequences associated with recA, namely A box, B box, a src-like phosphorylation site and a DNA binding site. Those skilled in the art will appreciate that, as was found for UmREC2, not all portions of a mREC2 protein are essential for the in vitro activities that characterize ATP-dependent homologous binding proteins. However, the region of about 120 amino acids from about residue 80 to residue 200, which is recA-like, is essential for these activities.

5.3 The Use of mREC2 and mREC2 Encoding Genes to Effect Homologous Recombination Between the Genome of a Cell and an Exogenous Nucleic Acid In one embodiment of the invention, a plasmid that expresses an mREC2 is used to increase the rate of homologous recombination between an exogenous nucleic acid and the genome of a cell. In one embodiment, the exogenous nucleic acid is a chimeric repair vector (CRV), which is an oligonucleotide having mixed ribo- and deoxyribonucleotides. The structure of CRV are disclosed in U.S. Pat. No. 556,350 filed Dec. 4, 1994, and U.S. Pat. No. 5,731,181 filed Jun. 17, 1996, which are hereby incorporated by reference in its entirety. U.S. Pat. No. 5,760,012 entitled "Methods and Compounds for Curing Diseases Caused by Mutations," filed May 1, 1996, by E. B. Kmiec, A. Cole-Strauss and K. Yoon, (the '517 Application), which is hereby incorporated by reference in its entirety, describes the use of CRV to repair mutations that cause diseases. Particularly, the '012 Patent concerns the repair of mutations that affect hematopoietic cells such as the mutation in β-globin that causes Sickle Cell Disease.

According to the present invention, the cell having a disease-causing mutation to be repaired (the target cell) is removed from the subject. The target cells are then transfected with a nucleic acid having a promoter operably linked to a nucleic acid encoding a mREC2 (an mREC2 expression vector) such that a mammalian ATP-dependent homologous pairing protein is over-expressed in the target cell. For most types of human cells, the immediate early promoter from cytomegalovirus is suitable. Because the persistent over-expression of a mammalian ATP-dependent homologous pairing protein can effect the growth and differentiation of the target cell, the mREC2 expression vector should be incapable of replication in the target cell. The mREC2 expression vector can be introduced into the target cell by any technique known to those in the field or to be developed. Liposomal compositions such as LIPOFECTIN(™) and DOTAP(™) are suitable.

After transfection with the mREC2 expression vector, the target cells are cultured for twenty four hours and then a CRV designed to repair the disease causing mutation is introduced into the target cells, according to the methods of the '517 Application, and repaired target cells are then reimplanted into the subject. Alternatively, the repaired target cells can be frozen and reimplanted at a clinically opportune time.

FIG. 5 shows the results of the use of an mREC2 expression vector to enhance the effectiveness of a CRV that repairs the mutation that causes Sickle Cell Disease in a human EB-transformed lymphoblastoid cell line. These data show that at a concentration of CRV of about 100 ng/ml, the pretreatment of the target cells with the mREC2 expression vector pcHsREC2, labelled "pchREC2" in FIG. 5, caused an about 5 fold increase, from 12% to 65%, in the percent of repaired copies of β-globin. At 250 ng/ml, over 80% of the copies of β-globin were repaired. At higher concentrations of CRV, the differences between pcHsREC2 treated target cells and control target cells become less marked.

The present invention is exemplified by the use of a non-replicating episome to introduce an mREC2 cDNA gene (hsREC2), operably linked to a cytomegalovirus (CMV) promoter, into the target cell and to transiently express mREC2. Alternative embodiments of the invention can be produced by introducing the copy of a genomic gene, which can be linked to the homologous mREC2 promoter or, alternatively, modified so that the homologous promoter is replaced by a CMV or other heterologous promoter. Further variants that can be used to increase homologous recombination in different situations include linkage of either mREC2 cDNA or gDNA to tissue specific promoters such as a CD4, immunoglobulin, insulin or globin promoter. By use of tissue specific promoters, transgenic animals, particularly mice, rats and swine can be constructed that overexpress mREC2 in only one particular tissue. In yet a further alternative embodiment the promoter can be an inducible promoter. An inducible promoter particularly suitable for the present invention is a tetracycline inducible promoter, which is described in U.S. Pat. No. 5,464,758, which is incorporated by reference in its entirety.

Those skilled in the art will further appreciate that an mREC2 encoding gene can be constructed that contains some but not all introns of the complete mREC2 gDNA. Such a gene is a mixture of mREC2 gDNA and mREC2 cDNA fragments. As used herein the term "an mREC2 gene" is to be understood to denote, generically, mREC2 cDNA, mREC2 gDNA or a nucleic acid encoding a full length REC2 protein comprising mREC2 gDNA and mREC2 cDNA fragments.

The present invention further encompasses the use of mREC2 expression vectors to facilitate the construction of transgenic animals using cultured embryonic stem cells ("ES cells") according to the method of Capecchi, M. R., 1989, Science 244: 1288 and U.S. Pat. No. 5,487,992, Col. 23–24, which are incorporated by reference in their entirety. A transgenic mouse having a inducible mREC2 gene introduced can be constructed. ES cells from such a transgenic mouse can be obtained and induced to have elevated levels of mREC2. Such cells will more readily undergo homologous recombination with a chimeric mutational vector ("CMutV"), an oligonucleotide having a similar structure and function to those of CRV, that can be used to introduce specific mutations into targeted wild-type genes. By use of CMutV, second and higher generation transgenic animals having further targeted genetic alterations can be constructed.

A further embodiment of the invention concerns the use of isolated and purified mREC2 protein in the construction of transgenic animals. Those skilled in the art of constructing transgenic animals understand that transgenic animals are constructed by direct injection of a nucleic acid into the pronucleus of an ovum according to the method described Brinster, R. L. et al., 1989, PROC. NATL. ACAD. SCI 86:7087; see also U.S. Pat. No.4,873,191 to T. E. Wagner and P. C. Hoppe, which are hereby incorporated by reference in their entirety. Such direct injection results in the random integration of the injected nucleic acid. As noted above techniques for the introduction of transgenes by homologous recombination have been developed, however, such techniques require a specialized embryonic stem cell line, which is available only for mice, and, in addition require that the genetic alteration be designed so that homologous recombinants can be selected in culture, since the rate of homologous recombination is very low.

Because the use of the present invention in conjunction with CMutV permits a specific alteration to be introduced into a large fraction, e.g., 80%, of the copies of a target gene, those skilled in the art will appreciate that the invention provides a practical technique for the construction of transgenic animals wherein the function of both alleles of a specifically targeted gene has been deleted ("knocked-out") by homologous recombination using ova directly injected with a REC2 CMutV mixture.

Transgenic animals are constructed according to the invention by injecting a ova pronucleii with mREC2 protein and the CMutV. In a preferred embodiment a mixture of the CMutV and a mREC2 protein is injected into the ova pronucleus. In a preferred embodiment the nucleic acid to be injected is a CMutV that introduces a stop codon or a frameshift mutation into the gene to be knocked out. The concentration of protein to be used is about one molecule of mREC2 protein per between 5,000 base pairs and 50 base pairs of the CMutV, preferably one molecule of mREC2 protein per about 100–500 base pairs of the CMutV. Alternatively, the CMutV can be replaced by a conventional linearized DNA fragment containing homologous regions flanking a mutator region.

5.4 The Construction of muREC2-Knock-out Mice

The invention additionally provides transgenic mice that contain inactivated muREC2. Such heterozygous muREC2-knock-out transgenic mice can be constructed by injection of a murine embryonic blastocyst with an embryonic stem cell line (ES cells) that has the appropriate mutation in muREC2 ($muREC2^{ko}$). The technique of Nichols, J.,et al., 1990, DEVELOPMENT 110:1341–48 can be used. Further teaching regarding the construction of transgenic mice using embryonic stem cell-injected blastocysts can be found in U.S. Pat. No. 5,487,992 to Capecchi and Thomas, which is hereby incorporated by reference in its entirety. Homozygous muREC2-knock-out mice can be obtained by the intercross of heterozygous muREC2-knock-out mice and selection of offspring that are homozygous for the $muREC2^{ko}$ allele.

Without limitation, a $muREC2^{ko}$, gene can be made in two ways. A CMutV can be constructed according to U.S. Pat. No. 5,565,350, which is designed to introduce one or more stop codons at different positions within muREC2 (an "$muREC2^{ko}$, chimeric vector"). ES cells line can be treated with the $muREC2^{ko}$, chimeric vector. Preferably several $muREC2^{Ko}$, chimeric vectors, designed to introduce redundant stop codons are used to reduce the reversion rate. After treatment, the ES cells can be cloned and the loss of a functional muREC2 gene confirmed by sequence analysis or by PCR amplification using primers specific for the mutated codons.

Alternatively, a dicistronic targeting construct can be used to introduce a $mUREC2^{ko}$ mutation. Mountford, P., et al., 1994, Proc. Natl. Acad. Sci. 91:4303–07. More specifically, targeting vector is constructed having a cassette consisting of, in 5' to 3' order, a splice acceptor site, the 500 bp internal ribosome entry site (IRES) from encephalomyocarditis virus (EMCV), a fusion gene ggeo, that has both β-galactosidase and G418 resistance activity, and an polyadenylation signal from SV40. In the targeting construct, the cassette is inserted, as an example without limitation, between two fragments from the introns 3' and 5' of the second exon of the muREC2 gene, wherein the 5' most exon is the first exon, the exon immediately 3' to the 5'-most exon is the second exon etc. The length of the fragments can be preferably between about 500 bp and 5,000 bp.

The linearized targeting construct can be introduced into an ES cells by any technique suitable for the transfection of DNA into ES cells. The muREC2 gene of the transfected ES cells undergoes homologous recombination whereby the cassette replaces the second exon such that the cassette is transcribed from the muREC2 promoter and the βgeo protein is translated by ribosomes bound to the IRES. ES cells having the cassette integrated into transcriptionally active genes can be selected by exposing the transfected cells to G418 and by histochemical staining to detect galactosidase positive cells. Typically as many as 70% to 90% of βgal⁺/neo$^r$ double transformants have undergone homologous recombination of the targeted gene.

Homozygous muREC2$^{ko}$ mice have an increased susceptibility to mutation caused by chemical and physical agents. Such animals can be used to determine if products are mutagenic and more specifically if such products are carcinogens. Both homozygous and heterozygous muREC2$^{ko}$ mice will also be more susceptible to the development of benign and malignant tumors. These animals can be used to originate tumors of different tissue types for use in biomedical studies.

5.5 The Classification of Samples of Human Tissue by Examination of the hsREC2 Genes of the Sample Those skilled in the art appreciate that there is a close connection between the a cell's capacity to remove chemically induced mutations and replication errors from its DNA and the cell's potential to develop the genetic changes that result in the development and progression of malignancies. Altonen, L. A., 1993, Science 260:812–816; Chung, D. C., & Rustgi, A. K., 1995, Gastroenterology 109:1685–99. A cell's capacity to remove mutations and replication errors can be classified by determining, firstly, whether the cell contains the normal, i.e., diploid number of copies of a gene that is essential for DNA mismatch repair and, secondly, by determining whether the copies that are present have been altered, i.e., contain mutations. Cells having a diminished capacity to remove DNA mismatches because of defects in their REC2 are malignant or are more likely to become malignant due to the further accumulation of mutations.

In one embodiment, the invention consists of classifying a human tissue according to the number of copies of the hsREC2 gene per diploid genome. The reduction of the number to less than two indicates that some cells of the tissue can have a reduced capacity to repair DNA mismatches, because a mutation in the remaining copy would cause the absence of ATP-dependent homologous pairing activity. The number of copies of a gene can be readily determined by quantitative genomic blotting using probes constructed from labelled nucleic acids containing sequences that are fragment of SEQ ID NO:2 or a complement therof. An alternative method of determining the number of hsRfC2 genes per diploid genome in a sample of tissue relies on the fact that the hsREC2 gene is located in bands 14q23–24 and, particularly, that it is tightly linked to the proximal side of the marker D14S258 and also tightly linked to the marker D14S251. The loss of a copy of a hsREC2 gene in an individual who is heterozygous at a locus linked to the D14S258 marker can be inferred from the loss of the heterozygosity.

An alternative embodiment of the invention consists of classifying a sample of human tissue according to whether or not it contains an unmutated copy of a hsREC2 gene. The hsREC2 gene of the sample and the hsREC2 of a standard tissue can be compared by any technique known to those skilled in the art or to be developed. A sensitive technique suitable for the practice of this embodiment of the invention is single strand conformational polymorphism (SSCP). Orita, M., et al., 1989, Genomics 5:874–879; Hayashi, K., 1991, PCR Methods and Applic. 1:34–38. The technique consists of amplifying a fragment of the gene of interest by PCR; denaturing the fragment and electrophoresing the two denatured single strands under non-denaturing conditions. The single strands assume a complex sequence-dependent intrastrand secondary structure that affects the strands electrophoretic mobility. Therefore comparison of an amplified fragment of a hsREC2 gene from a sample of tissue with the amplified fragment from a hsREC2 gene of a standard tissue is a sensitive technique for detecting mutations in the hsREC2 of the sample.

The absence of a copy of an unmutated hsREC2 gene in a sample of tissue indicates that the cells of the tissue have undergone or likely will undergo transformation into a malignant phenotype.

In a further alternative embodiment of the tissue sample can be classified by Southern blotting of the DNA of the sample. The presence of tissue specific bands in the blot is evidence that at least one copy of the REC2 gene of the sample has undergone a mutational event. In yet a further embodiment of the invention, the tissue sample can be classified by amplifying a fragment of the REC2 gene, by PCR, and analyzing the fragment by sequencing or by electrophoresis to determine if the sequence and length of the amplified fragment is that which can be expected from a normal REC2 gene.

Without limitation, particular types of tissue samples that can be classified according to the invention include tumors which are associated with cytogenetic abnormalities at bands 14q23–24. Such tumor types include renal cell carcinomas and ovarian cancers Mittelman, F., 1994, Catalog of Chromosome Aberrations in Cancer, (Johansson, B. and Mertens,F. eds.) Wiley-Liss, New York, pp 2303–2484. Also suitable for classification according to the method of the invention are tumor types that show a loss of heterozygosity of markers linked to the region 14q23–24. Such tumor types include meningiomas, neuroblastomas, astrocytomas and colon adenomas. Cox, D. W., 1994, Cytogenetic Cell Genet. 66:2–9. Of particular interest is the high rate of breast adenocarcinomas that have been found to have either mutated hsREC2 genes or to have lost heterozygosity of the microsatellite DNA at the closely linked locus D14S258.

In addition to the above described methods the embodiments of the invention include a kit comprising a pair of oligonucleotides suitable for use as primers to amplify a fragment of a hsREC2 gene, which pair consists of a 5'-primer having a sequence of a fragment of SEQ ID NO:2 and a 3'-primer having a sequence of a fragment of its complement wherein the 3'-primer is complementary to a portion of the sequence of SEQ ID NO:2 that lies 3' of the location of the 5'-primer sequence. The length of the 3' and 5'-primers is at least 12 nucleotides and preferably between about 16- and 25-nucleotides and more preferably between 18 and 24 nucleotides. The invention further consists of oligonucleotides having a sequence of a fragment of SEQ ID NO:2 or its complement and a label, which are suitable for hybridization with genomic blots of the hsREC2 gene. Labels include radiolabels such as $^{32}$P, fluorescent labels or any label known or to be developed that allows for the specific detection of a nucleic acid sequence.

The plasmid pcHsREC2, in which the hsREC2 cDNA is operably linked to a CMV immediate early promoter has been deposited on Aug. 20, 1996, in the ATCC, Rockville, Md., and accorded accession No. 97685. The plasmid was deposited under the name "pcHuREC2," but is referred to herein as pcHsREC2 for consistency. The plasmid pcHsREC2 is derived from commercially available plasmid pcDNA3 (Invitrogen, Inc.) and contains a 1.2 Kb insert that encodes hsREC2, which can be removed from pcHsREC2 by cutting with the restriction enzymes Xbal and Kpnl.

EMBL-3-type λphage clones, designated λ5A and λ1C, which contain a 12 Kb and 16 Kb fragment of the 5' and 3' region of the hsREC2 gene, respectively, were deposited on Aug. 20, 1996, as accession No. 97683 and No. 97682, respectively.

AFIXII type λphage clones, designated λ5D2a and λ7B1a, which contain a 14 Kb and 14.9 Kb fragment of the 5' and 3' region of the muREC2 gene of strain 129SVJ, respectively, were deposited on Aug. 22, 1996 and Aug. 20, 1996, as accession No. 97686 and No. 97684, respectively. The inserts of λ5D2a and λ7B1a are released by cutting with a NotI restriction enzyme.

5.6 The REC2 Promoter

The promoters of hsREC2 and muREC2 were cloned. The hs REC2 promoter was cloned by a two step PCR-based promoter walking technique. Briefly, blunt ended genomic fragements are made by digestion with DraI and SspI, in the first and second step respectively. The restriction fragments are ligated to adapters. A primary PCR amplification is performed using a gene specific primer from the 5' extreme of the gene and an adapter specific primer. A secondary PCR is performed using nested, gene and adapter specific primers. The first step, primary and secondary gene specific primers were 5-CAG ACG GTC ACA CAG CTC TTG TGA TAA-3' (SEQ ID NO:8) and 5'-ACC CAC TCG TTT TAG TTT CTT GCT AC-3 (SEQ ID NO:9), respectively. The second step promoter walking primary and secondary primers were 5'-TAG AGA GAG AGA GAG AGC GAG ACA G-3' (SEQ ID NO:10) and 5'-GTC GAC CAC GCG TGC CCT ATA G-3' (SEQ ID NO:11), respectively. The first step and second step fragments were 0.8 and 0.9 Kb in length respectively.

The muREC2 promoter was sequenced by digestion of the clone λ5D2a with XbaI. The promoter was found on the largest fragment, of about 7 Kb. The sequences of the hsREC2 and muREC2 are given in FIGS. 7A–7C and 7D–7F respectively.

The level of REC2 transcripts in cultured human foreskin fibroblasts had been shown to be increased when the cells were exposed to $^{137}$Cs irradiation. Several yeast genes have been identified that are radiation induceable and the radiation sensitive cis-acting conrol sequences from the promoters of such genes have been identified. See references cited in footnotes to Tables I–III. The sequence of the hsREC2 and muREC2 promoters were therefore inspected for the presence of such sequences. FIGS. 7A–7C and 7D–7F demonstrates that numerous such sequences were present. Tables I–III show the sequence of the yeast UV responsive elements, their positions in the yeast gene in which they are found and the reference to the scientific publication where they are described.

The radiation induceability of the hsREC2 gene was directly assayed using UV radiation and the luciferase reporter gene in transiently transfected HeLa cells. The hsREC2 promoter was operably linked to a luciferase reporter gene and to the SV40 enhancer, placed downstream of the poly A addition signal. Any strong enhancer can be used, e.g., the enhancer from Cytomegalovirus, Hepatitis B Virus, α-fetoprotein, Rous Sarcoma Virus or Simian Virus 40. In this construct hsREC2 promoter was, in the absence of radiation approximately as strong a promoter as the SV40 immediate early promoter. When the cells were UV irradiated (35 J/m$^2$ UV) the hsREC2 promter showed an approximate two to three fold increase in activity. See Section 6.8, below.

A radiation induceable promoter can be used to increase the susceptibility of cells to radiation as, for example, in conjunction with radiation therapy of a cancer. A construct containing a hsREC2 promoter operably linked to a "suicide gene", e.g., herpes thymidine kinase, can be introduced into mitotically active cells using a retrovirus based vector. A tumor can be irradiated and, simultaneously, gancyclovir, a DNA antimetabolite prodrug that is converted by herpes thymidine kinase, can be administered.

Those skilled in the art appreciate that the activity of the REC2 promoter can be further localized by testing the activity of the fragment after deletions having been made. A functional, radiation induceable promoter that is smaller than the fragment of FIGS. 7A–7C or 7D–7F can be found. Accordingly as used herein a human REC2 promoter and a murine REC2 promoter is defined as a DNA having the sequence found in FIGS. 7A–7C or 7D–7F, respectively, or a fragment thereof, wherein said fragment is a promoter in HeLa cells. The terms hsREC2 promoter and muREC2 promoter refer to DNA molecules having the sequences found in FIGS. 7A and 7B respectively. A REC2 promoter from any species can be defined analogously. Accordingly, in one embodiment, the invention concerns a composition containing only a defined number of types of DNA molecules, one of which molecules comprises a REC2 promoter. As used herein such composition is said to comprise an isolated and purified REC2 promoter. In an alternative embodiment, the invention concerns a plasmid having a bacterial origin of replication (henceforth a "cloning plasmid"), which plasmid comprises a mammalian REC2 promoter and specifically a human or a murine REC2 promoter. Those skilled in the art will further appreciate that the cis-acting radiation sensitive control elements present in the sequences of FIGS. 7A–7C and 7d–7F can identified by systematic testing of fragments having the appropriate deletions. Accordingly, there can be REC2 promoters, as defined above, that are less radiation induceable than the hsREC2 promoter. As used herein a mammalian REC2 promoter is said to radiation incduceable if the promoter shows at least a two fold increase in activity and a REC2 promoter is termed "three fold induceable" if it shows a three fold increase when tested under the conditions wherein hsREC2 gives at least a four fold increase.

In further embodiments the REC2 promoter is operably linked to a enhancer. The present invention is illustrated by use of the SV40 enhancer. Those skilled in the art appreciate that any enhancer that is as strong as the SV40 enhancer can be used. Alternative enhancers include Cytomegalovirus, Hepatitis B Virus, α-fetoprotein, Rous Sarcoma Virus or Simian Virus 40 enhancers.

TABLE I

UASs of *Saccharomyces cerevisiae* DNA repair genes

| Gene | Location | Sequences | SEQ ID NO | References |
|---|---|---|---|---|
| PHR1 | -103 | CGAGGAAGCAGT | 15 | 13,14 |
|  | -110 | CGAGGAAGAAAA | 16 |  |
| RAD2 | -166 | GGAGGCATTAAA | 17 | 5 |
| RAD23 | -295 | GGTGGCGAAATT | 18 | 15,16 |
| RAD51 | -215 | CGTTACCCTAT | 19 |  |
| RAD54 | -256 | CGTTACCCAAT | 24 |  |
| Consensus |  | GGAGGARRNANA | 20 |  |
|  |  | C T  C |  |  |

TABLE II

UASs of *Saccharomyces cerevisiae* DNA repair genes

| Gene | Location | Sequences | SEQ ID NO | References |
|---|---|---|---|---|
| Rhp51+ | −290 | CGTT_CCCTAT | 21 | 11 |
|  | −260 | CCTA_CCCTAA | 22 |  |
| RAD51 | −215 | CGTTACCCTAT | 23 | 12 |
| RAD54 | −256 | CGTTACCCAAT | 24 | 17 |
| RNR3 | −429 | CGGTTGCCATG | 25 | 18 |
| Consensus |  | CGTTACCCTAT | 26 |  |

TABLE III

URSs of *Saccharomyces cerevisiae* DNA repair genes

| Gene | Position | Sequences | SEQ ID NO | References |
|---|---|---|---|---|
| MAG | −215 | GTAGGTCGAA | 27 | 1 |
| PHR1 | −103 | CGAGGAAGCA | 28 | 2 |
|  | −109 | CGAGGAAGAA | 29 | 2 |
| RAD2 | −169 | CGTGGAGGCA | 30 | 1,2,3,4,5 |
| RAD51 | −157 | CGTGGTGGGA | 31 | 6,12 |
| DDR48 | −271 | CGAGGATGAC | 32 | 1,7 |
|  | −322 | CGTGGTTGAT | 33 | 1,7 |
| RNR2 | −374 | CGAGGTCGCA | 34 | 8,9 |
| RNR3 | −467 | CTAGGTAGCA | 35 | 1,10 |
| rhp51+ | −233 | GTAGGTGTTA | 36 | 11 |
|  | −213 | CTAGGTAACA | 37 | 11 |
| RAD16 | −309 | CATGGTTGCC | 38 | 1 |
| Consensus |  | CGTGGTNGAA A A CC | 39 | 1 |

References to Tables I–III
1. Xiao W. et. at., 1993, Mol. Cell. Biol., 13, 7213–7221
2. Sebastian. J. et. al., 1990, Mol. Cell. Biol., 10, 4630–4637
3. Madura, K. et. al., 1986, J. Bacteriol., 166, 914–923
4. Reynolds, P. et. al., 1985, EMBO J.,.4, 3549–3552
5. Siede, W. et. al., 1989, Mol. Microbiol., 3, 1697–1707
6. Basile, G. et. al., 1992, Mol. Cell. Biol., 12, 3235–3246
7. Treger, J. M. et. al.,1990, Mol. Cell. Biol., 10, 3174–3184
8. Elledge, S. J. et. al., 1989, Mol. Cell. Biol., 9, 5373–5386
9. Hurd, H. K. et. al., 1989, Mol. Cell. Biol., 9, 5359–5372
10. Yagle, K. et. al., 1990, Mol. Cell. Biol., 10, 5553–5557
11. Jang, Y. K. et. al., May 23, 1996, Molecular & General Genetics, 251 (2),167–175,
12. Aboussekhra A. et. al, 1992, Mol. Cell. Biol., 12, 3224–3234
13. Sancar, G. B., 1985, Nucleic Acids Research, 13, 8231–8246
14. Sancar, G. B. et. al., 1995, Nucleic Acids Research, 23, 4320–4328
15. Jones, J. S. et. al., 1991, Nucleic Acids Research, 19, 893–898
16. Watkins, J. F. et. al., 1993, Mol. Cell. Biol., 13, 7757–7765
17. Cole, G. M. et. al., 1989, Mol. Cell. Biol., 9, 3314–3322
18. Elledge S. J. et. al., 1989a, Mol. Cell. Biol., 7, 4932–4940

5.7 REC2-Transfectants are Sensitized to Irradiation

One embodiment of the present invention is a plasmid or other isolated purified DNA molecule in which a mREC2 cDNA is operably linked to a strong promoter, which is preferably a constitutive promoter, e.g., a CMV immediate early promoter. In a further embodiment the invention consists of a mammlian cell that is transfected with such plasmid or isolated purified DNA amd which over expresses Rec2. The overexpression of Rec2 causes a mammalian cells to be hypersensitive to DNA damaging agents such as alkylating agents, e.g., cyclophosphamide, γ-ray or UV-irradiation.

Accordingly, the present invention can be used to sensitize a set of cells that can be selectively transfected with a Rec2 expressing plasmid. Such sensitization can be used in conjunction with conventional oncologic chemotherapy or irradiation therapy to treat malignant disease.

6. EXAMPLES

6.1

The Production of Recombinant hsREC2 Protein by Baculovirus Infection of *Autographica Californica*

To facilitate the construction of an hsREC2 expression vector, restriction sites for Xhol and Kpnl were appended by PCR amplification to a the hsREC2 cDNA. The hsREC2 cDNA starting at nt 71 was amplified using the forward primer 5'-GAG CTCGAG GGTACC C ATG GGT AGC AAG AAA C-3' (SEQ ID NO:14), which placed the Xhol and Kpnl sites (underlined) 5' of the start codon. The recombinant molecule containing the entire coding sequence of hsREC2 cDNA, can be removed using either Xhol or Kpnl and the unique Xbal site located between nt 1270 and 1280 of SEQ ID NO:2.

A vector, pBacGSTSV, for the expression of HsREC2 in baculovirus infected *Spodoptera frugiperda* (Sf-9) insect cells (ATCC cell line No. CRL1711, Rockville Md.), was obtained from Dr. Zailin Yu (Baculovirus Expression Laboratory, Thomas Jefferson University). The vector pVLGS was constructed by the insertion of a fragment encoding a *Schistosoma japonicum* glutathione S-transferase polypeptide and a thrombin cleavage site from pGEX-2T (described in Smith & Johnson, GENE 67:31 (1988)), which is hereby incorporated by reference, into the vector into the vector pVL1393. A polyA termination signal sequence was inserted into pVLGS to yield pBacGSTSV. A plasmid containing the 1.2 Kb hsREC2 fragment was cut with Kpnl, the 3' unpaired ends removed with T4 polymerase and the product cut with Xbal. The resultant fragment was inserted into a Smal, Xbal cut pBacGSTSV vector to yield pGST/hsREC2.

Recombinant virus containing the insert from pGST/hsREC2 were isolated in the usual way and Sf-9 cells were infected. Sf-9 cells are grown in SF900IISFM (Gibco/BRL Cat # 10902) or TNM-FH (Gibco/BRL Cat # 11605-110) plus 10% FBS. After between 3–5 days of culture the infected cells are collected, washed in $Ca^{++}$ and $Mg^{++}$ free PBS and sonicated in 5 ml of PBS plus proteinase inhibitors (ICN Cat # 158837), 1% NP-40, 250 mM NaCl per $5 \times 10^7$ cells. The lysate is cleared by centrifugation at 30,000×g for 20 minutes. The supernatant is then applied to 0.5 ml of glutathione-agarose resin (Sigma Chem. Co. Cat # G4510) per $5 \times 10^7$ cells. The resin is washed in a buffer of 50 mM Tris-HCl, pH 8.0, 150 mM NaCl and 2.5 mM $CaCl_2$, and the hsREC2 released by treatment with thrombin (Sigma Chem. Co. Cat # T7513) for 2 hours at 23° C. in the same buffer. For certain experiments the thrombin is removed by the technique of Thompson and Davie, 1971, Biochim Biophys Acta 250:210, using an aminocaproyl-p-chlorobenzylmide affinity column (Sigma Chem. Co. Cat # A9527).

6.2 Detection of the Enzymatic Properties of hsREC2 Protein

Baculovirus produced hexahistidylhsREC2 was tested in a DNA reannealing assay as described in Kmiec, E. B., & Holloman, W. K., 1982, Cell 29:367–74. The results, FIG. 3, showed that hsREC2 catalyzes the reannealing of denatured DNA. An optimal reaction occurred at about 1 hsREC2 per 50–100 nucleotides.

Further studies to characterize hsREC2 showed that it catalyzes the reaction ATP→ADP+PO$_4$. Similar to recA, at ATP concentrations of <100 μM, there is cooperativity between hsREC2 molecules; the Hill coefficient (1.8) suggests that the functional unit for ATP hydrolysis is at least a dimer. Gel retardation experiments were performed to determine the ATP dependence of hsREC2 binding to ssDNA. The results of these experiments showed that hsREC2 binds ssDNA only in the presence of ATP or its non-hydrolyzable thio analog γ-SATP. FIG. 4. Again the hsREC2 results parallel those of recA. Further examples of specific assays using isolated and purified hsRec2 are as follows:

6.2.1 Binding to Single Stranded DNA

A 73 nucleotide single stranded DNA (SS) was $^{32}$P end labelled using polynucleotide kinase. DNA binding was carried out using 0.25 ng of labeled SS in 25 mM Tris-HCl, pH 7.4, 10 mM MgCl$_2$, 4 mM ATP, and 1 mM DTT and protein. hsRec2-thioredoxin was partially purified on a Thiobond™ column (Invitrogen) and desalted/concentrated using a Microcon 30 spin column (Amicon). Approximately 0.3 μg protein was added. The reaction mixture was incubated 30 min. at 37° C., following which sucrose was added to facilitate loading onto a polyacrylamide gel. The mixture was loaded onto a 12% nondenaturing gel in 90 mM Tris, 90 mM borate, pH 8.3, 2 mM EDTA for 3 hours at 150 V. The gel was then dried and exposed overnight. Approximately 3% of the label was retarded in the presence of ATP or γS-ADP, while reduced amounts of label were bound in the absence of either of ATP or γS-ADP.

6.2.2 Catalysis of Reannealing of DNA

Reannealing of a 123 nucleotide fragment was determined as follows. The single stranded 123 nucleotide (SS) was $^{32}$P end labelled using polynucleotide kinase. Varying amounts of affinity purified GST-hsRec2 fusion protein was added to 0.5 ng of SS in 25 μl of 20 mM TrisHCl pH 7.5, 10 mM MgCl$_2$, 0.5 mM DTT with 5 mM ATP optionally present. Samples were incubated 30 min. at 37° C., followed by phenol/chloroform extraction to stop the reaction, followed by a second 30 min. incubation at 37° C. The reaction mixture was then electrophoresed as in section 6.2.1, above, and autoradiographed. The results, shown in FIG. 6, demonstrate that GST-hsREC2 catalyzes the reannealing of the SS in both the presence and absence of ATP.

6.3 Overexpression of hsREC2 Suppresses UVC-Induced Mutation

To determine whether the presence of hsRec2 protects cultured cells from UVC induced mutation a CHO cell line was transfected with a mixture of linearized pcHsREC2 and pCMVneo and a clone resistant to G418 was selected ("15C8 hsREC2"). Elevated levels of hsREC2 expression were confirmed by immunoblotting using rabbit antisera raised to baculovirus produced hsRec2 fusion proteins.

Mutability was determined as follows. 1.6×10$^6$ 15C8 hsREC2 cells were plated in a 100 mm petri dish and exposed to 0 or between 2.0 and 5.0 J/m$^2$ UV radiation. After 7 days of culture, the remaining cells were exposed to 40 μM 6-TG. Surviving cells had undergone an inactivation of the HPRT gene. After a further 7–10 days of culture the number of colonies was counted. The mutation frequency was adjusted for the cloning efficiency of the population which was determined by plating a limiting number of cells without 6-TG.

The results showed that the untransfected, pCMVneo and 15C8 hsREC2 cells had mutation rates of 1.7, 6.2 and 0.4 per million, respectively, without UVC irradiation. After UVC radiation the mutation rates observed were, in three experiments, between 94 and 16, 61 and 74, and 3 and 37, per million, for untransfected, pCMV transfected and 15C8 hsREC2 cells, respectively. Thus, the expression of hsREC2 caused a marked decrease in the susceptibility of CHO cells to UVC induced mutation as well as a drop in the spontaneous mutation frequency.

6.4 Enhanced Repair of β-globin in Cultured, EB-transformed Human Lymphoblasts

SC1, a chimeric vector designed to repair the mutation found in Sickle Cell Disease β-globin, contained two blocks of ten 2'-O-methyl RNA residues each, flanking an intervening block of five DNA residues, see FIG. 5B. When the molecule was folded into the duplex conformation, one strand contained only DNA residues while the other strand contained the RNA/DNA blocks. In this case, the internal sequence is complementary to the β$^S$ globin sequence over a stretch of 25 residues that span the site of the β$^S$ mutation, with the exception of a single base (T) which is in bold and designated with an asterisk. The five DNA residues flanked by RNA residues were centered about the mutant T residue in the β$^S$ coding sequence. Genomic sequences of the β$^A$, β$^S$, and closely-related δ-globin genes are also displayed in FIG. 3 with the specific site of β$^S$ mutation printed in bold.

Lymphoblastoid cells were prepared as follows. Heparin-treated blood was obtained from discarded clinical material of a patient with sickle cell disease. Mononuclear cells were prepared from blood (≅8 ml) by density gradient centrifugation in Ficoll and infected with Epstein-Barr virus which had been propagated in the marmoset cell line B95-8 (Coriell Institute for Medical Research #GM07404D). Infections were performed with addition of 0.1 mg leucoagglutinin PHA-L in 10 ml RPMI medium supplemented with 20% fetal bovine serum in a T25 flask. Cultures were fed twice a week starting on day 5 and were considered established once 60–70% of the cells remained viable at day 21. The β$^A$ and β$^S$ lymphoblastoid cells were maintained in RPMI medium containing 10% fetal bovine serum.

The EBV-transformed lymphoblastoid cells were transiently transfected with either the vector pcDNA3 or the vector having inserted hsREC2 cDNA (pcHsREC2). Transfection was done using mixtures of 15 μl DOTAP and 2.5 μg DNA, as detailed below. After transfection the cells were incubated for 24 hours and then treated with varying amounts of SC1.

SC1 was introduced into the above-described lymphoblastoid cells homozygous for the β$^S$ allele as follows. Cells (1×10$^5$ per ml) were seeded in 1 ml of medium in each well of a 24-well tissue culture plate the day prior to the experiment. Transfections were performed by mixing chimeric oligonucleotides in amounts ranging from 0 to 250 ng, with 3 μl of DOTAP (N-[1-(2,3-Dioleoyloxy)propyl]-N,N,N-trimethylammonium methylsulfate, Boehringer-Mannheim) in 20 ml of 20 mM HEPES, pH 7.3, incubated at room temperature for 15 min, and added to the cultured cells. After 6 h the cells were harvested by centrifugation, washed and prepared for PCR amplification following the procedure of E. S. Kawasaki, PCR Protocols, Eds. M. A. Innis, D. H. Gelfand, J. J. Sninsky and T. J. White, pp146–152, Academic Press, (1990).

Correction of the single base mutation was assessed by taking advantage of well known restriction fragment length polymorphisms resulting from the β$^S$ mutation, R. F. Greeves et al., 1981, Proc. Natl. Acad. Sci. 78:5081; J. C. Chang and Y. W. Kan, 1982, N. Eng. J. Med. 307:30; S. H. Orkin et al., ibid., p. 32; J. T. Wilson et al., 1982, Proc. Natl. Acad. Sci. 79:3628. The A to T transversion in the β$^S$ allele results in the loss of a Bsu361 restriction site (CCTGAGG). Thus, the β$^S$ allele can be detected by Southern hybridization analysis of genomic DNA cut with Bsu36I. A 1.2 Kb Bsu36I DNA fragment of the β-globin gene present normally is absent in the $\beta^S$ allele and is replaced by a diagnostic 1.4 Kb fragment. When genomic DNA recovered from homozygous $\beta^S$ lymphoblastoid cells was analyzed by this procedure, the expected 1.4 Kb fragment was observed. However, two fragments were observed in DNA from cells transfected with the SC1 CRV. The presence of the 1.2 Kb fragment in addition to the 1.4 Kb fragment indicates partial correction of the $\beta^S$ allele had taken place in a dose-dependent fashion.

The results of the experiment are shown in FIG. 5A. At 100 ng and 250 ng of SC1 between 65% and 85% of the $\beta^S$ alleles were mutated to $\beta^A$ alleles in the cells pre-transfected with pcHsREC2, compared to between 10% and 25% in the non pre-transfected cells and negligible levels in the control transfected cells. At levels of SC1 between 25 ng and 50 ng of SC1, no mutations were detected in any of the control cell populations while between 30% and 40% of the $\beta^S$ alleles were mutated to $\beta^A$ alleles in the cells pre-transfected with pcHsREC2.

These results show that the over expression of hsREC2 causes marked increase in the susceptibility of a cell to mutation by a chimeric mutation vector such as SC1.

6.5 Identification and Isolation of mREC2 gDNA Clones

Genomic blots of human and murine, strain 129 SVJ, DNA were made using XbaI and BamHI digests. Following transfer to Zeta-Probe™ membranes (Bio-Rad) the membranes were prehybridized for 30' at 55° C. in 0.25M NaHPO$_4$, pH7.2, 7% SDS, 1 mM EDTA and hybridized overnight with a random primed full length HsREC2 probe. Wash was 2× for 20' at 42° C. in 0.04M NaHPO$_4$, pH7.2, 5% SDS, 1 mM EDTA and 1× each at 42° C. and 50° C. for 20' in 0.04M NaHPO$_4$, pH 7.2, 1% SDS, 1 mM EDTA. The results were bands of the following sizes: Human-XbaI 6.0, 4.1, 2.6, 2.0 and 1.5 Kb; Human-BamHI 9.5, 8.5, 6.5, 4.6, 1.5 Kb; Murine-XbaI 9.0, 6.0, 4.1, 3.5, 1.9, 0.8 Kb; and Murine-BamHl 8.0, 2.7 and 1.8.

To identify and propagate clones containing mREC2 from cDNA or DNA libraries standard techniques for cloning were employed using λ-phage libraries. A human genome library in EMBL-3 and a murine genomic library in λFIXII were screened. Phage plaques were transferred to hybridization filters by standard techniques and the filters were probed with radiolabelled hsREC2 cDNA. After hybridization the filters were washed. A wash consisting of twice at 42° C. for 20' in 2×SSC, 0.1% SDS followed by thrice at 50° C. for 20' in the same solution was used to isolate murine gDNA clones. To isolate human gDNA clones a the wash procedure was: twice 20 min. at 42° C. in 40 mM NaHPO$_4$, pH 7.2, 1 mM EDTA, and 5% SDS; followed by once for 20 min. at 50° C. in the same solution except for 1% SDS.

The 5' and 3' fragments of muREC2 and hsREC2 gDNA were recovered in the following λphage clones: λ5D2a (14 Kb insert, 5' muREC2); λ7B1a (14.9 Kb insert, 3' muREC2); λ5A (12 Kb insert, 5' hsREC2); λ1C (16 Kb insert, 3' hsREC2), each of which has been deposited in the ATCC, Bethesda, Md.

Fragments of genomic clones can be used as probes of genomic blots to identify rearrangements deletions or other abnormalities of hsREC2 in tumor cells. Those skilled in the art further appreciate that by routine sequence analysis and comparison with the sequence of SEQ ID NO: 2, the boundaries of the exons and introns of hsREC2 can be identified. Knowing the sequence of at the intron/exon boundaries allows for the construction of PCR suitable for the amplification and analysis of each exon as alternatives to the methods of section 6.6.

6.6 Elevated Incidence of Abnormalities in hsREC2 in Adenocarcinomas of the Breast Samples of 30 primary ductal carcinoma of the breast were analyzed by Southern blot, probed with the hsREC2 cDNA and by a high resolution gel of the PCR product of the microsatellite marker D14S258, which is closely linked to the hsREC2 gene. Ten of the thirty samples gave abnormal results in one of the two assays and 3 showed abnormalities by both assays. In contrast none of 16 samples of primary renal cell carcinoma showed clear abnormalities in a Southern blot.

6.6.1 Loss of Heterozygosity of Microsatellite DNA Linked to hsREC2

The location of hsREC2 was found to be tightly linked to the proximal side of the microsatellite marker D14S258. Because there is extensive polymorphism in the lengths of microsatellite sequences most individuals are heterozygous at the D14S258 locus. Primers specific for unique sequences flanking the polymorphic locus can be used to generate PCR fragments whose length is allele specific. Primers specific for D14S258 were obtained from the Dr. Lincoln Stein, Whitehead Institute, MIT, Cambridge Mass. The "5'" primer is 5'-TCACTGCATCTGGAAGCAC-3' (SEQ ID NO:12) and the "3'" primer is 5'-CTAACTAAATGGC-GAGCATTGAG-3' (SEQ ID NO:13). PCR was performed with a genomic DNa concentration of 2.0 ng/μl, a primer concentration of 10.0 μM, 10.0 μM dNTP, 500 μM Tris HCl, pH 9.2, 17.5 μM MgCl$_2$, 160 μM (NH$_4$)$_2$SO$_4$, and a polymerase concentration of 0.03 U/μl. Amplification was performed for 35 cycles of 50 seconds each, alternating between 57° C. and 94° C., followed by an extension of 7 minutes at 72° C. and preceded by an initial heat soak of 5 minutes at 94° C. The expected product is about 160–170 nucleotides in length.

A comparison of the products of PCR amplification of tumor and normal tissue control DNA using the flanking primers can reveal the loss of either or both D14S258 loci, which suggests that the linked hsREC2 has also been lost.

The results of analysis 7 of 30 samples breast tumors showed a complete or partial loss of one allele at locus D14S258.

These results show that instability and loss of a genetic locus tightly linked to the location of hsREC2 is found in a large fraction of human ductal adenocarcinoma of the breast.

6.6.2 Frequent Rearrangements of hsREC2

Genomic DNA from samples of 16 primary renal and 30 primary breast tumors tumor tissue were digested with either XbaI or BamHl restriction enzymes, electrophoresed in a 0.8% agarose gels and processed for hybridization with labeled random primed copies made from the hsREC2 cDNA. After transfer, Zetaprobe™ blotting membranes were UV crosslinked, prehybridized at 65° C. for 20 min in 0.25M NaHPO$_4$, pH 7.4, 7% SDS, 1 mM EDTA and then hybridized overnight under the same conditions. The membranes were pre-washed once with 40 mM NaHPO$_4$, pH 7.2, 5% SDS, 1 mM EDTA at 42° C. for 20 min, then washed repeatedly at 60° C. in the same solution, except for 1% SDS, until background levels were achieved in the periphery of the membrane. The filters were then exposed to film.

Six of the 30 examples of carcinoma of the breast showed rearrangements or abnormalities while none of the 16 samples of renal cell carcinoma showed clear rearrangements.

6.7 Construction of a MuREC2$^{ko}$ Containing ES Cell Line

The muREC2 gDNA clone λ5D2a contains the first two exons. The second exon is located on 3.6 Kb Eco R1 fragment, approximately 1.2 Kb from the fragment's 5' border. The secnd exon contains a unique Stu1 site into which was inserted the IRES-βgeo poly A cassette, Mountford, P., et al., 1994, Proc. Natl. Acad. Sci. 91, 4303–4307. ES cells were cultured on primary mouse embroyo fibroblasts according to standard protocols, Hogan, B., et al., 1996, Manipulating the Mouse Embryo, Cold Spring Harbor Press. Approximately $2 \times 10^7$ ES cells were transfected by electroporation with 25 μg linearized DNA. Selection was begun at 36 hours and continued until day 8 with 250 μg/ml G418. Thirty colonies were isolated and tested by Xba1 digest and Southern blot; one colony was found to lack the wild type size Xba1 fragment and to have a novel fragment of the predicted size. Transgenic mice are constructed from this ES cell line by conventional techniques. Ibid.

6.8 The HsREC2 Promoter Is Radiation Induceable

A 1.8 Kb fragment immediately 5' to the hsREC2 start codon was cloned. The fragment was tested as a promoter using the luciferase reported gene construct, pGL2, (Promega Cat. No. E1611), luciferase activity was measured using the luciferase reported test kit (Boehringer Mannheim Cat. No. 1669 893).

The activity of the promoter is assayed in HeLa cells as follows. The HeLa cels are trypsinized on day −1 and plated at $6.6 \times 10^5$/60 mm well in 3.0 ml of DMEM. On day two at −1 h the medium is replaced with serum free medium and the cells are transfected with various quantities of the plasmid with DOSPER at a DNA:DOSPER ratio of 1:4. At 5 hour an additional 3.0 ml of medium supplemented with FBS is added; at 24 hours the cells are irradiated with UV light (Stratalinker). Cells are harvested at 48 hours and proteins extracted and assayed. Control experiments done with the same plasmid having the SV40 immediate early promoter in place of the hsREC2 promoter.

| UV Irradiation | DNA Added (Micrograms) | | | |
|---|---|---|---|---|
| (Joules meter$^2$) | 3 μg | 2.4 μg | 1.2 μg | 0.6 μg |
| 0J m$^2$ | 655.6[1] | 494[2] | 27.5 | 32.8 |
| 15J m$^2$ | 951.5 | 1287 | 28.9 | 28.7 |
| 25J m$^2$ | 1033.6 | 1398 | 35.8 | 44.2 |
| 35J m$^2$ | 1134.6 | 1786 | 84.89 | 68.4 |

[1]The corresponding luciterase is 513.9 pSV40-luc-SV40 enhancer at 0 Joules meter$^2$.
[2]The corresponding luciferase is 384 pSV40-luc-SV40 enhancer at 0 Joules meter$^2$.

When the 3' 0.8 Kb of the hsREC2 promoter was tested beginning with nt 869 of SEQ ID NO: 5, it was determined that this 0.8 Kb fragment contains a promoter having reduced activity but which is also shows an about 5 fold induceability with 35 j/m$^2$ UV radiation in HCT 116, which cell line contains a normal p53 gene. The preferred form of the REC2 induceable promoter in HCT 116 is the shortened form starting at nt 869.

6.9 The Expression of REC2 Causes Increased Radiation Sensitivity

UV irradiation induces apoptosis in stable transfectants expressing wild-type HsRec2 but not truncated or full length with an altered tyrosine 163 site. In order to measure the effects of REC2 expression on the rate of UV induced radiation CHO cells were irradiated. During the 24 hour long recovery period following irradiation, more CHO cells expressing wild-type HsRec2 were observed to die than the control cells that expressed an irrelevant or nonfunctional proteins. To determine whether cell death was a result of apoptosis, asynchronous cells were irradiated at a dose of 15 j/m$^2$, and fixed in ethanol at 24, 48 and 72 hours following irradiation. FACS analysis was conducted as folows: Cells were trypsinized, washed once with PBS and fixed in 70% ethanol at least 30 minutes at 4° C. Cell pellets were treated with DNase-free Rnase for 30 minutes at 70° C. at a final concentration of 0.16 mg/ml and stained in propidium iodide (0.05 mg/ml) for 15 minutes, then stored overnight prior to analysis by FACS. The FACS analysis and determination of the percentage of cells in G1, S and G2 phases (Multicycle Flow program) was carried out in the Cell Cycle Center at the Kimmel Cancer Institute of Thomas Jefferson University. Cells from duplicate cultures were harvested at the same time points, and frozen at −80° C. for DNA isolation. DNA was isolated using a QIAGEN Blood Kit (QIAGEN Inc., Chatsworth, Calif.) and stored at 4° C. until run on gels. DNA was run o 1% agarose gels in TAE buffer and stained 30 minutes with a 1:10,000 dilution of SYBR Green I (FMC, Rockland, Me.). Gels were then scanned using a FluorImager (Molecular Diagnostics, San Diego, Calif.).

Four cell types were used for analysis; CHO cells containing the empty vector (Neo$^r$), CHO cells expressing HsRec2Δ103–350 (3D2), HsRec2$^{ala63}$ (PH4), and the wild-type HsRec2 (15C8). A sub-G1 population was detected at 24, 48, and 72 hours following irradiation for CHO cells expressing the wild-type HsRec2 only. To confirm that apoptosis was occurring, DNA was isolated from cells, and run on a 1% agarose gel, stained with SYBR Green I and scanned. For each time interval compared, 15C8 exhibited a more pronounced ladder than the other clones. Although there appears to be a small amount of apoptosis for the clone expressing HsRec2$^{ala63}$ it is considerably lower than for the wild-type HsRec2 clone, and neither the Neo$^r$ or the transfectants expressing the truncated protein are comparable. Therefore, the G1 delay and apoptosis require the wild-type HsRec2, and suggests that perhaps cooperation between a mutant p53 present in CHO cells and Rec2 may be responsible for genome surveillance in these cells.

The results of the FACS analysis of the HsRec2 expressing and the Neo$^r$ expressing clones are given in FIGS. 8A–8H.

What is claimed is:

1. A method of classifying a sample of human tissue for a decrease in susceptibility to UVC-induced mutation, the method comprising:
   (1) quantifying the copies of hsREC2 per diploid genome of the sample tissue; and
   (2) comparing the quantity of hsREC2 per diploid genome of the sample tissue with the quantity of hsREC2 per diploid genome of a standard tissue which contains the normal number of copies of hsREC2 per diploid genome,
   wherein an increase in the quantity of hsREC2 per diploid genome in the sample tissue compared to the quantity of hsREC2 in the standard tissue indicates a decrease of the human tissue to susceptibility to UVC-induced mutation.

2. The method of claim 1, wherein the sample is a sample of a breast.

3. The method of claim 1, wherein the sample is a sample of a colon.

4. The method of claim 1 wherein the quantification of the copies of hsREC2 is performed by measuring the lengths of microsatellite DNA at marker D14S258 and comparing the sizes present in the sample tissue and the sizes present in the standard tissue, provided the standard tissue and the sample tissue are from the same subject.

5. The method of claim 1, wherein the method further comprises the step of amplifying a fragment of a hsREC2 gene, and wherein the amplification step is a polymerase chain reaction that employs a primer consisting of a sequence of at least 12 contiguous nucleotides of SEQ ID NO: 2 or the complement thereof.

6. The method of claim 5, wherein the primer consists of a sequence of not more than 25 contiguous nucleotides of SEQ ID NO: 2 or the complement thereof.

7. A kit comprising:
   a. a first separate nucleic acid fragment which consists of a sequence of at least 12 contiguous nucleotides of SEQ ID NO: 2; and
   b. a second separate nucleic acid fragment which consists of a sequence of at least 12 contiguous nucleotides of the complement of SEQ ID NO: 2;
   wherein the second sequence is complementary to a portion of SEQ ID NO: 2 that is 3' to the first sequence.

8. A composition for the amplification of a fragment of an hsREC2 gene comprising a nucleic acid fragment which consists of at least 12 contiguous nucleotides of SEQ ID NO: 2 or the complement thereof and a DNA polymerase.

9. The composition of claim 8, in which the sequence of the fragment consists of between 12 and 25 contiguous nucleotides of SEQ ID NO:2 or the compliment thereof.

10. A method of screening a subject for an increased susceptibility to developing adenocarcinoma of the breast, the method comprising detecting a loss of heterozygosity of the D14S258 marker in a sample of breast tissue from the subject, wherein detection of a loss of heterozygosity at the D14S258 marker indicates an increased susceptibility of the subject to developing adenocarcinoma of the breast.

* * * * *